(12) United States Patent
Boudreaux

(10) Patent No.: US 9,993,284 B2
(45) Date of Patent: Jun. 12, 2018

(54) ELECTROSURGICAL INSTRUMENT WITH JAW CLEANING MODE

(71) Applicant: Ethicon Endo-Surgery, Inc., Cincinnati, OH (US)

(72) Inventor: Chad P. Boudreaux, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 423 days.

(21) Appl. No.: 14/576,860

(22) Filed: Dec. 19, 2014

(65) Prior Publication Data
US 2016/0175022 A1    Jun. 23, 2016

(51) Int. Cl.
*A61B 18/08*    (2006.01)
*A61B 18/14*    (2006.01)
(Continued)

(52) U.S. Cl.
CPC ........ *A61B 18/085* (2013.01); *A61B 18/1445* (2013.01); *A61B 2017/0088* (2013.01); *A61B 2018/00005* (2013.01); *A61B 2018/0063* (2013.01); *A61B 2018/00136* (2013.01); *A61B 2018/00404* (2013.01); *A61B 2018/00482* (2013.01); *A61B 2018/00601* (2013.01); *A61B 2018/00607* (2013.01);
(Continued)

(58) Field of Classification Search
CPC ............ A61B 18/1442; A61B 18/1445; A61B 18/1447; A61B 2018/1452; A61B 2018/145; A61B 2018/1455; A61B 2018/1457; A61B 2018/146; A61B 2018/1462
See application file for complete search history.

(56) References Cited

U.S. PATENT DOCUMENTS 4,805,823 A    2/1989  Rothfuss
5,415,334 A    5/1995  Williamson et al.
(Continued)

FOREIGN PATENT DOCUMENTS

EP    2 151 204 A1    2/2010
EP    2 371 315 A1    10/2011

OTHER PUBLICATIONS

U.S. Appl. No. 61/410,603, filed Nov. 5, 2010.
(Continued)

*Primary Examiner* — Ronald Hupczey, Jr.
*Assistant Examiner* — Tigist Demie
(74) *Attorney, Agent, or Firm* — Frost Brown Todd LLC

(57) ABSTRACT

An apparatus for operating on tissue comprises an end effector disposed at the distal end of an elongate shaft and including a first jaw and a second jaw that is selectively pivotable toward and away from the first jaw to capture tissue. A trigger is configured to move the second jaw toward and away from the first jaw. The locking mechanism in the locked state is configured to allow movement of the second jaw along a first path where a relative angle between the first jaw and the second jaw is limited to a first maximum angle. The locking mechanism in the unlocked state is configured to allow movement of the second jaw along a second path where the relative angle between the first jaw and the second jaw is limited to a second maximum angle. The second maximum angle is greater than the first maximum angle.

20 Claims, 13 Drawing Sheets

(51) Int. Cl.
  *A61B 18/00* (2006.01)
  *A61B 17/00* (2006.01)
  *A61B 90/00* (2016.01)
(52) U.S. Cl.
  CPC ............... *A61B 2018/00815* (2013.01); *A61B 2018/00875* (2013.01); *A61B 2018/00892* (2013.01); *A61B 2018/00898* (2013.01); *A61B 2018/00922* (2013.01); *A61B 2018/00982* (2013.01); *A61B 2018/1455* (2013.01); *A61B 2090/0813* (2016.02); *A61B 2218/008* (2013.01)

(56) References Cited

U.S. PATENT DOCUMENTS

| | | | |
|---|---|---|---|
| 5,465,895 A | 11/1995 | Knodel et al. | |
| 5,597,107 A | 1/1997 | Knodel et al. | |
| 5,632,432 A | 5/1997 | Schulze et al. | |
| 5,673,840 A | 10/1997 | Schulze et al. | |
| 5,704,534 A | 1/1998 | Huitema et al. | |
| 5,814,055 A | 9/1998 | Knodel et al. | |
| 6,500,176 B1 | 12/2002 | Truckai et al. | |
| 6,783,524 B2 | 8/2004 | Anderson et al. | |
| 6,978,921 B2 | 12/2005 | Shelton et al. | |
| 7,000,818 B2 | 2/2006 | Shelton et al. | |
| 7,112,201 B2 | 9/2006 | Truckai et al. | |
| 7,125,409 B2 | 10/2006 | Truckai et al. | |
| 7,143,923 B2 | 12/2006 | Shelton et al. | |
| 7,169,146 B2 | 1/2007 | Truckai et al. | |
| 7,186,253 B2 | 3/2007 | Truckai et al. | |
| 7,189,233 B2 | 3/2007 | Truckai et al. | |
| 7,220,951 B2 | 5/2007 | Truckai et al. | |
| 7,303,108 B2 | 12/2007 | Shelton | |
| 7,309,849 B2 | 12/2007 | Truckai et al. | |
| 7,311,709 B2 | 12/2007 | Truckai et al. | |
| 7,354,440 B2 | 4/2008 | Truckai et al. | |
| 7,367,485 B2 | 5/2008 | Shelton et al. | |
| 7,380,695 B2 | 6/2008 | Doll et al. | |
| 7,380,696 B2 | 6/2008 | Shelton et al. | |
| 7,381,209 B2 | 6/2008 | Truckai et al. | |
| 7,404,508 B2 | 7/2008 | Smith et al. | |
| 7,343,715 B2 | 10/2008 | Ito et al. | |
| 7,434,715 B2 | 10/2008 | Shelton et al. | |
| 7,540,872 B2* | 6/2009 | Schechter | .......... A61B 18/1445 606/50 |
| 7,628,791 B2 | 12/2009 | Garrison et al. | |
| 7,721,930 B2 | 5/2010 | McKenna et al. | |
| 8,408,439 B2 | 4/2013 | Huang et al. | |
| 8,453,914 B2 | 6/2013 | Laurent et al. | |
| 8,461,744 B2 | 6/2013 | Wiener et al. | |
| 8,603,134 B2 | 12/2013 | Twomey et al. | |
| 8,888,809 B2 | 11/2014 | Davison et al. | |
| 8,939,974 B2 | 1/2015 | Boudreaux et al. | |
| 8,951,248 B2 | 2/2015 | Messerly et al. | |
| 8,956,349 B2 | 2/2015 | Aldridge et al. | |
| 8,986,302 B2 | 3/2015 | Aldridge et al. | |
| 9,039,695 B2 | 5/2015 | Giordano et al. | |
| 9,050,093 B2 | 6/2015 | Aldridge et al. | |
| 9,060,776 B2 | 6/2015 | Yates et al. | |
| 9,089,327 B2 | 7/2015 | Worrell et al. | |
| 9,089,360 B2 | 7/2015 | Messerly et al. | |
| 9,113,940 B2 | 8/2015 | Twomey | |
| 9,161,803 B2 | 10/2015 | Yates et al. | |
| 9,220,559 B2 | 12/2015 | Worrell et al. | |
| 9,402,682 B2 | 8/2016 | Worrell et al. | |
| 2006/0079874 A1 | 4/2006 | Faller et al. | |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2012/0078243 A1 | 3/2012 | Worrell et al. | |
| 2012/0078244 A1 | 3/2012 | Worrell et al. | |
| 2013/0023868 A1 | 1/2013 | Worrell et al. | |

OTHER PUBLICATIONS

U.S. Appl. No. 61/550,768, filed Oct. 24, 2011.
International Search Report dated Jul. 19, 2016 for Application No. PCT/US2015/065507, 8 pgs.
International Preliminary Report on Patentability and Written Opinion dated Jun. 20, 2017 for Application No. PCT/US2015/065507, 9 pgs.

* cited by examiner

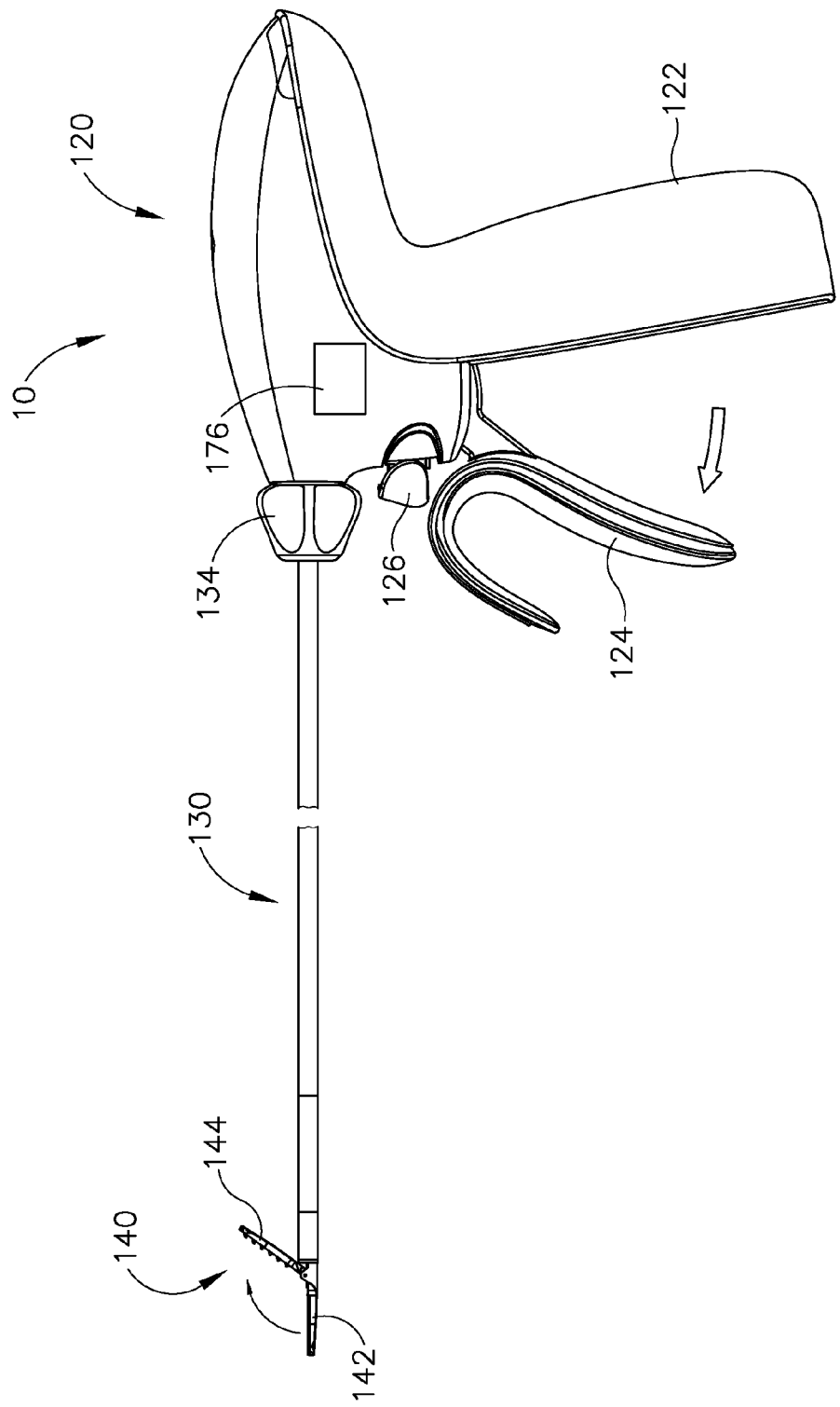

ELECTROSURGICAL INSTRUMENT WITH JAW CLEANING MODE

BACKGROUND

A variety of surgical instruments include a tissue cutting element and one or more elements that transmit radio frequency (RF) energy to tissue (e.g., to coagulate or seal the tissue). An example of such an electrosurgical instrument is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical cutting instruments and related concepts are disclosed in U.S. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein; U.S. Pat. No. 8,888,809, entitled "Surgical Instrument with Jaw Member," published Nov. 18, 2014, the disclosure of which is incorporated by reference herein; U.S. Pub. No. 2012/0116379, entitled "Motor Driven Electrosurgical Device with Mechanical and Electrical Feedback," published May 10, 2012, now U.S. Pat. No. 9,161,803, issued Oct. 20, 2015, the disclosure of which is incorporated by reference herein; U.S. Pub. No. 2012/0078243, entitled "Control Features for Articulating Surgical Device," published Mar. 29, 2012, now U.S. Pat. No. 9,877,720, issued Jan. 30, 2018, the disclosure of which is incorporated by reference herein; U.S. Pub. No. 2012/0078247, entitled "Articulation Joint Features for Articulating Surgical Device," published Mar. 29, 2012, now U.S. Pat. No. 9,402,682, issued Aug. 2, 2016, the disclosure of which is incorporated by reference herein; U.S. Pub. No. 2013/0030428, entitled "Surgical Instrument with Multi-Phase Trigger Bias," published Jan. 31, 2013, now U.S. Pat. No. 9,089,327, issued Jul. 28, 2015, the disclosure of which is incorporated by reference herein; and U.S. Pub. No. 2013/0023868, entitled "Surgical Instrument with Contained Dual Helix Actuator Assembly," published Jan. 31, 2013, now U.S. Pat. No. 9,545,253, issued Jan. 17, 2017, the disclosure of which is incorporated by reference herein.

While a variety of surgical instruments have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 6B depicts a side elevational view of the instrument of FIG. 6A, showing the end effector in an extended open configuration.

Figure 1:
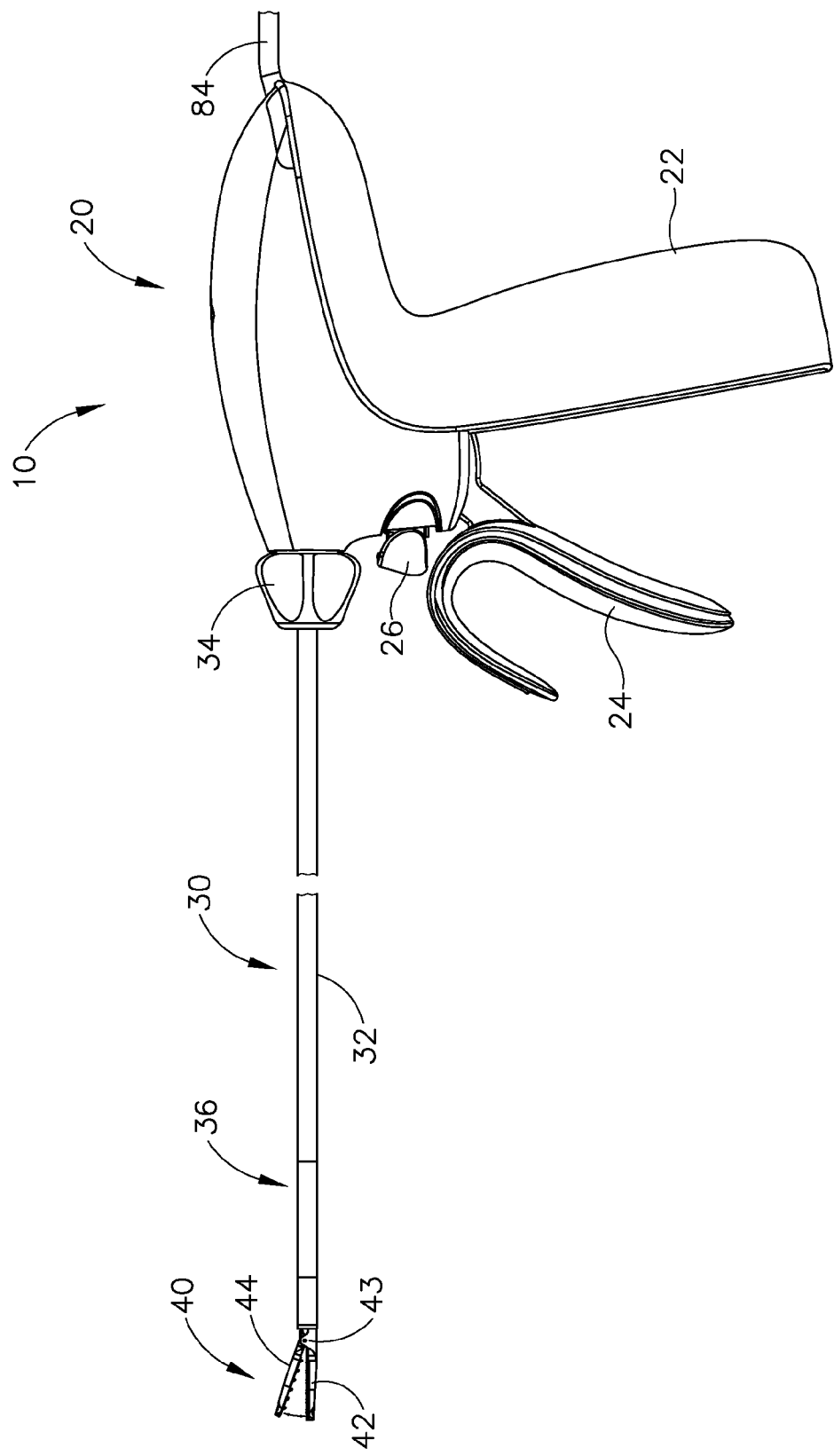
FIG. 1 depicts a side elevational view of an exemplary electrosurgical medical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

I. Exemplary Electrosurgical Device with Articulation Feature

FIGS. 1-4 show an exemplary electrosurgical instrument (10) that is constructed and operable in accordance with at least some of the teachings of U.S. Pat. No. 6,500,176; U.S. Pat. No. 7,112,201; U.S. Pat. No. 7,125,409; U.S. Pat. No. 7,169,146; U.S. Pat. No. 7,186,253; U.S. Pat. No. 7,189,233; U.S. Pat. No. 7,220,951; U.S. Pat. No. 7,309,849; U.S. Pat. No. 7,311,709; U.S. Pat. No. 7,354,440; U.S. Pat. No. 7,381,209; U.S. Pub. No. 2011/0087218, now U.S. Pat. No. 8,939,974, issued Jan. 27, 2015; U.S. Pub. No. 2012/0083783, now U.S. Pat. No. 8,888,809, issued Nov. 18, 2014; U.S. Pub. No. 2012/0116379, now U.S. Pat. No. 9,161,803, issued Oct. 20, 2015; U.S. Pub. No. 2012/0078243, now U.S. Pat. No. 9,877,720, issued Jan. 30, 2018; U.S. Pub. No. 2012/0078247, now U.S. Pat. No. 9,402,682, issued Aug. 2, 2016; U.S. Pub. No. 2013/0030428, now U.S. Pat. No. 9,089,327, issued Jul. 28, 2015; and/or U.S. Pub. No. 2013/0023868, now U.S. Pat. No. 9,545,253, issued Jan. 17, 2017. As described therein and as will be described in greater detail below, electrosurgical instrument (10) is operable to cut tissue and seal or weld tissue (e.g., a blood vessel, etc.) substantially simultaneously. In other words, electrosurgical instrument (10) operates similar to an endocutter type of stapler, except that electrosurgical instrument (10) provides tissue welding through application of bipolar RF energy instead of providing lines of staples to join tissue. It should also be understood that electrosurgical instrument (10) may have various structural and functional similarities with the ENSEAL® Tissue Sealing Device by Ethicon Endo-Surgery, Inc., of Cincinnati, Ohio. Furthermore, electrosurgical instrument (10) may have various structural and functional similarities with the devices taught in any of the other references that are cited and incorporated by reference herein. To the extent that there is some degree of overlap between the teachings of the references cited herein, the ENSEAL® Tissue Sealing Device by Ethicon Endo-Surgery, Inc., of Cincinnati, Ohio, and the following teachings relating to electrosurgical instrument (10), there is no intent for any of the description herein to be presumed as admitted prior art. Several teachings below will in fact go beyond the scope of the teachings of the references cited herein and the ENSEAL® Tissue Sealing Device by Ethicon Endo-Surgery, Inc., of Cincinnati, Ohio.

A. Exemplary Handpiece and Shaft

Electrosurgical instrument (10) of the present example includes a handpiece (20), a shaft (30) extending distally from handpiece (20), and an end effector (40) disposed at a distal end of shaft (30). Handpiece (20) of the present example includes a pistol grip (22), a pivoting trigger (24), and an activation button (26). Trigger (24) is pivotable toward and away from pistol grip (22) to selectively actuate end effector (40) as will be described in greater detail below. Activation button (26) is operable to selectively activate RF circuitry that is in communication with end effector (40), as will also be described in greater detail below. In some versions, activation button (26) also serves as a mechanical lockout against trigger (24), such that trigger (24) cannot be fully actuated unless button (26) is being pressed simultaneously. Examples of how such a lockout may be provided are disclosed in one or more of the references cited herein. In addition or in the alternative, trigger (24) may serve as an electrical and/or mechanical lockout against button (26), such that button (26) cannot be effectively activated unless trigger (24) is being squeezed simultaneously. It should be understood that pistol grip (22), trigger (24), and button (26) may be modified, substituted, supplemented, etc. in any suitable way, and that the descriptions of such components herein are merely illustrative.

Shaft (30) of the present example includes a rigid outer sheath (32) and an articulation section (36). Articulation section (36) is operable to selectively laterally deflect end effector (40) at various angles relative to the longitudinal axis defined by sheath (32). In some versions, articulation section (36) and/or some other portion of outer sheath (32) includes a flexible outer sheath (e.g., a heat shrink tube, etc.) disposed about its exterior. Articulation section (36) of shaft (30) may take a variety of forms. By way of example only, articulation section (36) may be configured in accordance with one or more teachings of U.S. Pub. No. 2012/0078247now U.S. Pat. No. 9,402,682, issued Aug. 2, 2016, the disclosure of which is incorporated by reference herein. As another merely illustrative example, articulation section (36) may be configured in accordance with one or more teachings of U.S. Pub. No. 2012/0078248, entitled "Articulation Joint Features for Articulating Surgical Device," published Mar. 29, 2012, now U.S. Pat. No. 9,220,559, issued Dec. 29, 2015, the disclosure of which is incorporated by reference herein. Various other suitable forms that articulation section (36) may take will be apparent to those of ordinary skill in the art in view of the teachings herein. It should also be understood that some versions of instrument (10) may simply lack articulation section (36).

In some versions, shaft (30) is also rotatable about the longitudinal axis defined by sheath (32), relative to handpiece (20), via a knob (34). Such rotation may provide rotation of end effector (40) and shaft (30) unitarily. In some other versions, knob (34) is operable to rotate end effector (40) without rotating articulation section (36) or any portion of shaft (30) that is proximal of articulation section (36). As another merely illustrative example, electrosurgical instrument (10) may include one rotation control that provides rotatability of shaft (30) and end effector (40) as a single unit; and another rotation control that provides rotatability of end effector (40) without rotating articulation section (36) or any portion of shaft (30) that is proximal of articulation section (36). Other suitable rotation schemes will be apparent to those of ordinary skill in the art in view of the teachings herein. Of course, rotatable features may simply be omitted if desired.

Although not shown, it should be understood that in some examples instrument (10) may include an articulation control (not shown). In such examples, the articulation control may be operable to selectively control articulation section (36) of shaft (30), to thereby selectively laterally deflect end effector (40) at various angles relative to the longitudinal axis defined by shaft (30). In some examples the articulation control may be in the form of a rotary dial. In other examples, the articulation control may take numerous other forms. By way of example only, some merely illustrative forms that the articulation control and other components of handpiece (20) may take are disclosed in U.S. Pub. No. 2012/0078243, now U.S. Pat. No. 9,877,720, issued Jan. 30, 2018, the disclosure of which is incorporated by reference herein; in U.S. Pub. No. 2012/0078244, entitled "Control Features for Articulating Surgical Device," published Mar. 29, 2012, now abandoned, the disclosure of which is incorporated by reference herein; and in U.S. Pub. No. 2013/0023868, now U.S. Pat. No. 9,545,253, issued Jan. 17, 2017, the disclosure of which is incorporated by reference herein. Still other suitable forms that the articulation control may take will be apparent to those of ordinary skill in the art in view of the teachings herein. It should also be understood that some versions of instrument (10) may simply lack the articulation control.

B. Exemplary End Effector

End effector (40) of the present example comprises a first jaw (42) and a second jaw (44). In the present example, first jaw (42) is substantially fixed relative to shaft (30); while second jaw (44) pivots relative to shaft (30), toward and away from first jaw (42). Use of the term "pivot" should not be read as necessarily requiring pivotal movement about a fixed axis. In some versions, second jaw (44) pivots about an axis that is defined by a pin (or similar feature) that slides along an elongate slot or channel as second jaw (44) moves toward first jaw (42). In such versions, the pivot axis translates along the path defined by the slot or channel while second jaw (44) simultaneously pivots about that axis. It should be understood that such sliding/translating pivotal movement is encompassed within terms such as "pivot," "pivots," "pivotal," "pivotable," "pivoting," and the like. Of course, some versions may provide pivotal movement of second jaw (44) about an axis that remains fixed and does not translate within a slot or channel, etc.

In some versions, actuators such as rods or cables, etc., may extend through sheath (32) and be joined with second jaw (44) at a pivotal coupling (43), such that longitudinal movement of the actuator rods/cables/etc. through shaft (30) provides pivoting of second jaw (44) relative to shaft (30) and relative to first jaw (42). Of course, jaws (42, 44) may instead have any other suitable kind of movement and may be actuated in any other suitable fashion. By way of example only, and as will be described in greater detail below, jaws (42, 44) may be actuated and thus closed by longitudinal translation of a firing beam (60), such that actuator rods/cables/etc. may simply be eliminated in some versions.

Figure 2:
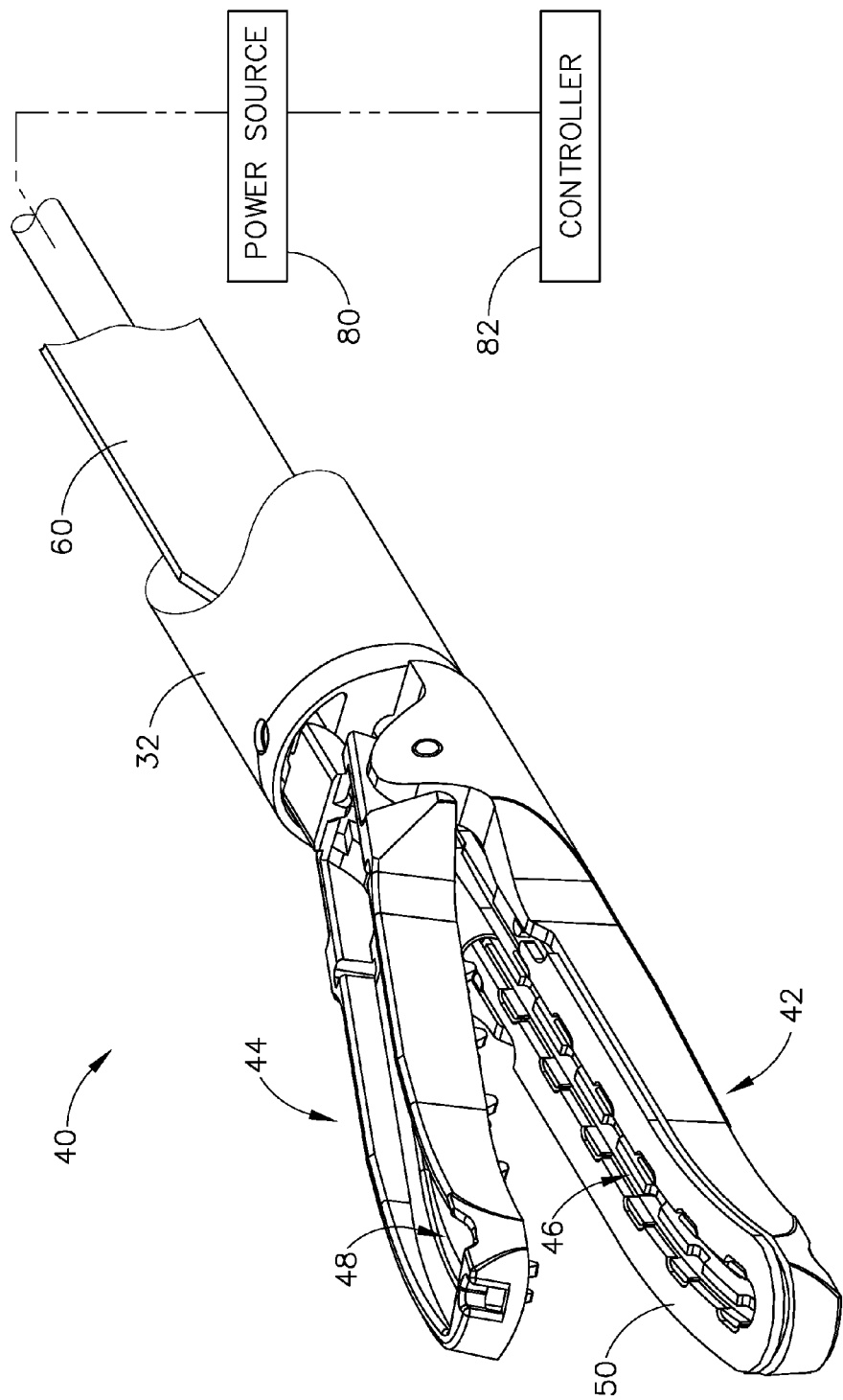
FIG. 2 depicts a perspective view of an end effector of the instrument of FIG. 1, in an open configuration.
Figure 3:
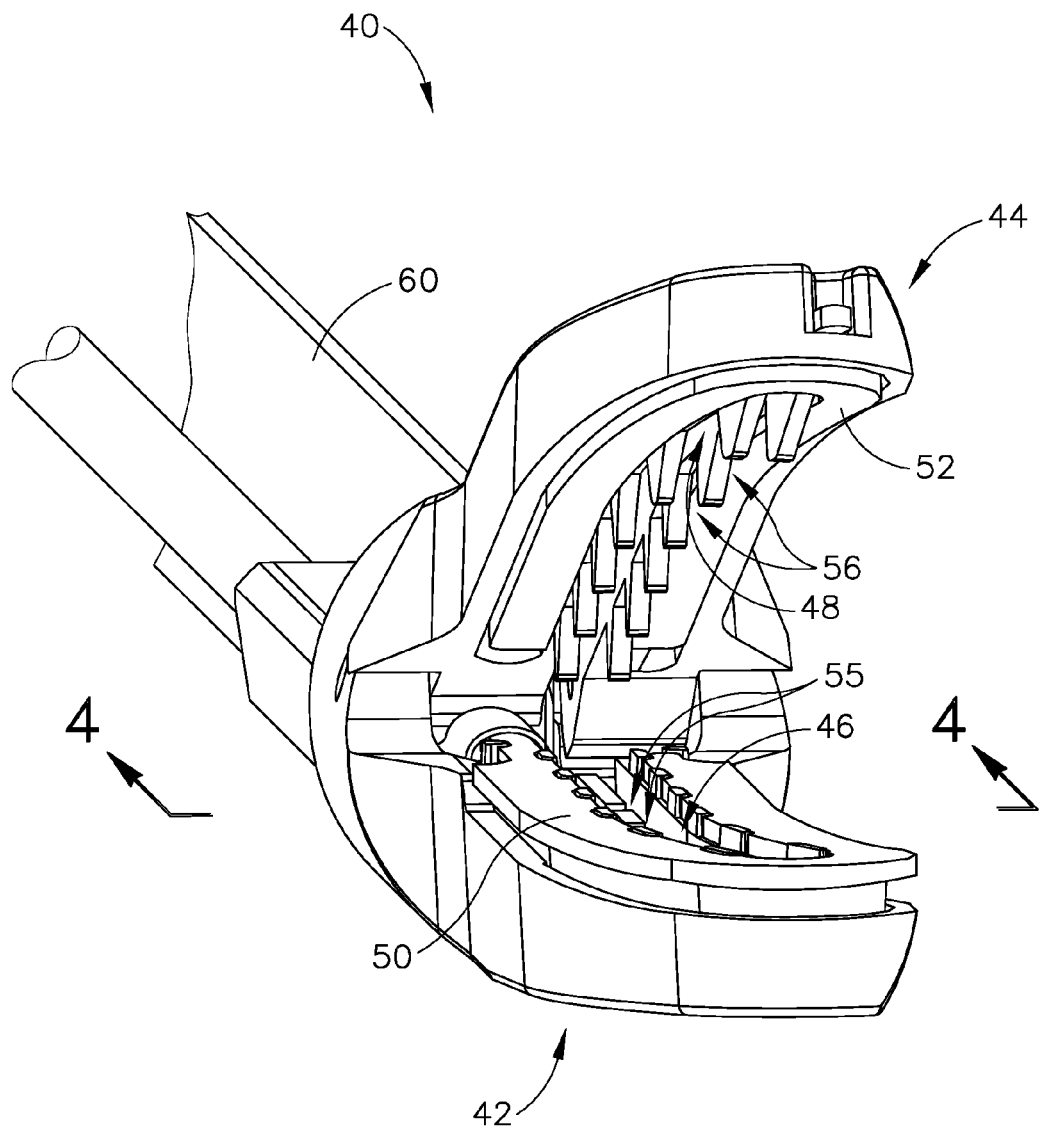
FIG. 3 depicts another perspective view of the end effector of the instrument of FIG. 1, in an open configuration.
Figure 4:
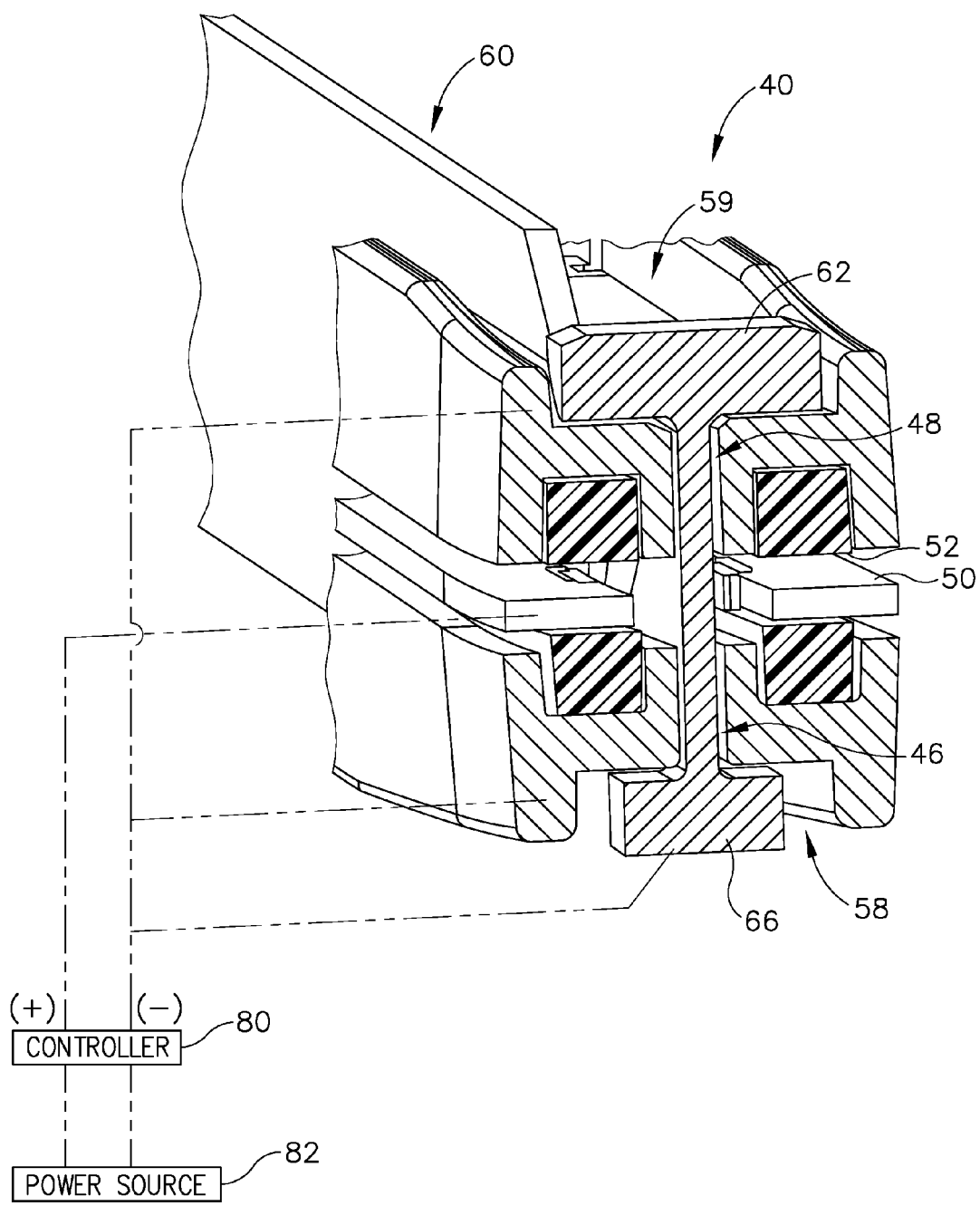
FIG. 4 depicts a cross-sectional end view of the end effector of FIG. 2, taken along line 4-4 of FIG. 3, in a closed configuration and with the firing beam in a distal position.

As best seen in FIGS. 2-4, first jaw (42) defines a longitudinally extending elongate slot (46); while second jaw (44) also defines a longitudinally extending elongate slot (48). In addition, the top side of first jaw (42) presents a first electrode (50); while the underside of second jaw (44) presents a second electrode (52). Electrodes (50, 52) are in communication with an electrical source (80) via one or more conductors (not shown) that extend along the length of shaft (30). These conductors are coupled with electrical source (80) and a controller (82) via a cable (84), which extends proximally from handpiece (20). Electrical source (80) is operable to deliver RF energy to first electrode (50) at an active polarity while second electrode (52) serves as a reference/return passive electrode, such that RF current flows between electrodes (50, 52) and thereby through tissue captured between jaws (42, 44). There are instances where the active signal crosses zero potential that the reference is at the same potential so there is no current flow. In some versions, firing beam (60) serves as an electrical conductor that cooperates with electrodes (50, 52) (e.g., as a ground return) for delivery of bipolar RF energy captured between jaws (42, 44). Electrical source (80) may be external to electrosurgical instrument (10) or may be integral with electrosurgical instrument (10) (e.g., in handpiece (20), etc.), as described in one or more references cited herein or otherwise. A controller (82) regulates delivery of power from electrical source (80) to electrodes (50, 52). Controller (82) may also be external to electrosurgical instrument (10) or may be integral with electrosurgical instrument (10) (e.g., in handpiece (20), etc.), as described in one or more references cited herein or otherwise. It should also be understood that electrodes (50, 52) may be provided in a variety of alternative locations, configurations, and relationships.

By way of example only, power source (80) and/or controller (82) may be configured in accordance with at least some of the teachings of U.S. Provisional Pat. App. No. 61/550,768, entitled "Medical Instrument," filed Oct. 24, 2011, the disclosure of which is incorporated by reference herein; U.S. Pub. No. 2011/0082486, entitled "Devices and Techniques for Cutting and Coagulating Tissue," published Apr. 7, 2011, now U.S. Pat. No. 9,089,360, issued Jul. 28, 2015, the disclosure of which is incorporated by reference herein; U.S. Pub. No. 2011/0087212, entitled "Surgical Generator for Ultrasonic and Electrosurgical Devices," published Apr. 14, 2011, now U.S. Pat. No. 8,986,302, issued Mar. 24, 2015, the disclosure of which is incorporated by reference herein; U.S. Pub. No. 2011/0087213, entitled "Surgical Generator for Ultrasonic and Electrosurgical Devices," published Apr. 14, 2011, now U.S. Pat. No. 8,951,248, issued Feb. 10, 2015, the disclosure of which is incorporated by reference herein; U.S. Pub. No. 2011/0087214, entitled "Surgical Generator for Ultrasonic and Electrosurgical Devices," published Apr. 14, 2011, now U.S. Pat. No. 9,039,695, issued May 26, 2015, the disclosure of which is incorporated by reference herein; U.S. Pub. No. 2011/0087215, entitled "Surgical Generator for Ultrasonic and Electrosurgical Devices," published Apr. 14, 2011, now U.S. Pat. No. 9,050,093, issued Jun. 9, 2015, the disclosure of which is incorporated by reference herein; U.S. Pub. No. 2011/0087216, entitled "Surgical Generator for Ultrasonic and Electrosurgical Devices," published Apr. 14, 2011, now U.S. Pat. No. 8,956,349, issued Feb. 17, 2015, the disclosure of which is incorporated by reference herein; and/or U.S. Pub. No. 2011/0087217, entitled "Surgical Generator for Ultrasonic and Electrosurgical Devices," published Apr. 14, 2011, now U.S. Pat. No. 9,060,776, issued Jun. 23, 2015, the disclosure of which is incorporated by reference herein. Other suitable configurations for power source (80) and controller (82) will be apparent to those of ordinary skill in the art in view of the teachings herein.

As best seen in FIG. 4, the lower side of first jaw (42) includes a longitudinally extending recess (58) adjacent to slot (46); while the upper side of second jaw (44) includes a longitudinally extending recess (59) adjacent to slot (48). FIGS. 2 and 3 show the upper side of first jaw (42) including a plurality of teeth recesses (55). Correspondingly, the lower side of second jaw (44) includes complementary teeth serrations (56) that nest within recesses (55), to enhance gripping of tissue captured between jaws (42, 44) without necessarily tearing the tissue. In other words, it should be understood that serrations (56) may be generally blunt or otherwise atraumatic. Although FIG. 3 shows first jaw having recesses (55) and second jaw (44) serrations (56) as, it should be understood that recesses (55) and serrations (56) may take any other suitable form or may be simply omitted altogether. It should also be understood that serrations (56) may be formed of an electrically non-conductive, or insulative, material, such as plastic, glass, and/or ceramic, for example, and may include a treatment such as polytetrafluoroethylene, a lubricant, or some other treatment to substantially prevent tissue from getting stuck to jaws (42, 44). In some versions, serrations (56) are electrically conductive.

With jaws (42, 44) in a closed position, shaft (30) and end effector (40) are sized and configured to fit through trocars having various inner diameters, such that electrosurgical instrument (10) is usable in minimally invasive surgery, though of course electrosurgical instrument (10) could also be used in open procedures if desired. By way of example only, with jaws (42, 44) in a closed position, shaft (30) and end effector (40) may present an outer diameter of approximately 5 mm. Alternatively, shaft (30) and end effector (40) may present any other suitable outer diameter (e.g., between approximately 2 mm and approximately 20 mm, etc.).

As another merely illustrative variation, either jaw (42, 44) or both of jaws (42, 44) may include at least one port, passageway, conduit, and/or other feature that is operable to draw steam, smoke, and/or other gases/vapors/etc. from the surgical site. Such a feature may be in communication with a source of suction, such as an external source or a source within handpiece (20), etc. In addition, end effector (40) may include one or more tissue cooling features (not shown) that reduce the degree or extent of thermal spread caused by end effector (40) on adjacent tissue when electrodes (50, 52) are activated. Various suitable forms that such cooling features may take will be apparent to those of ordinary skill in the art in view of the teachings herein.

In some versions, end effector (40) includes one or more sensors (not shown) that are configured to sense a variety of parameters at end effector (40), including but not limited to temperature of adjacent tissue, electrical resistance or impedance of adjacent tissue, voltage across adjacent tissue, forces exerted on jaws (42, 44) by adjacent tissue, etc. By way of example only, end effector (40) may include one or more positive temperature coefficient (PTC) thermistor bodies (not shown) (e.g., PTC polymer, etc.), located adjacent to electrodes (50, 52) and/or elsewhere. Data from sensors may be communicated to controller (82). Controller (82) may process such data in a variety of ways. By way of example only, controller (82) may modulate or otherwise change the RF energy being delivered to electrodes (50, 52), based at least in part on data acquired from one or more sensors at end effector (40). In addition or in the alternative, controller (82) may alert the user to one or more conditions via an audio and/or visual feedback device (e.g., speaker, lights, display screen, etc.), based at least in part on data acquired from one or more sensors at end effector (40). It should also be understood that some kinds of sensors need not necessarily be in communication with controller (82), and may simply provide a purely localized effect at end effector (40). For instance, the PTC thermistor bodies at end effector (40) may automatically reduce the energy delivery at electrodes (50, 52) as the temperature of the tissue and/or end effector (40) increases, thereby reducing the likelihood of overheating. In some such versions, a PTC thermistor element is in series with power source (80) and electrode (50, 52); and the PTC thermistor provides an increased impedance (reducing flow of current) in response to temperatures exceeding a threshold. Furthermore, it should be understood that electrodes (50, 52) may be used as sensors (e.g., to sense tissue impedance, etc.). Various kinds of sensors that may be incorporated into electrosurgical instrument (10) will be apparent to those of ordinary skill in the art in view of the teachings herein. Similarly various things that can be done with data from sensors, by controller (82) or otherwise, will be apparent to those of ordinary skill in the art in view of the teachings herein. Other suitable variations for end effector (40) will also be apparent to those of ordinary skill in the art in view of the teachings herein.

C. Exemplary Firing Beam

Figure 5:
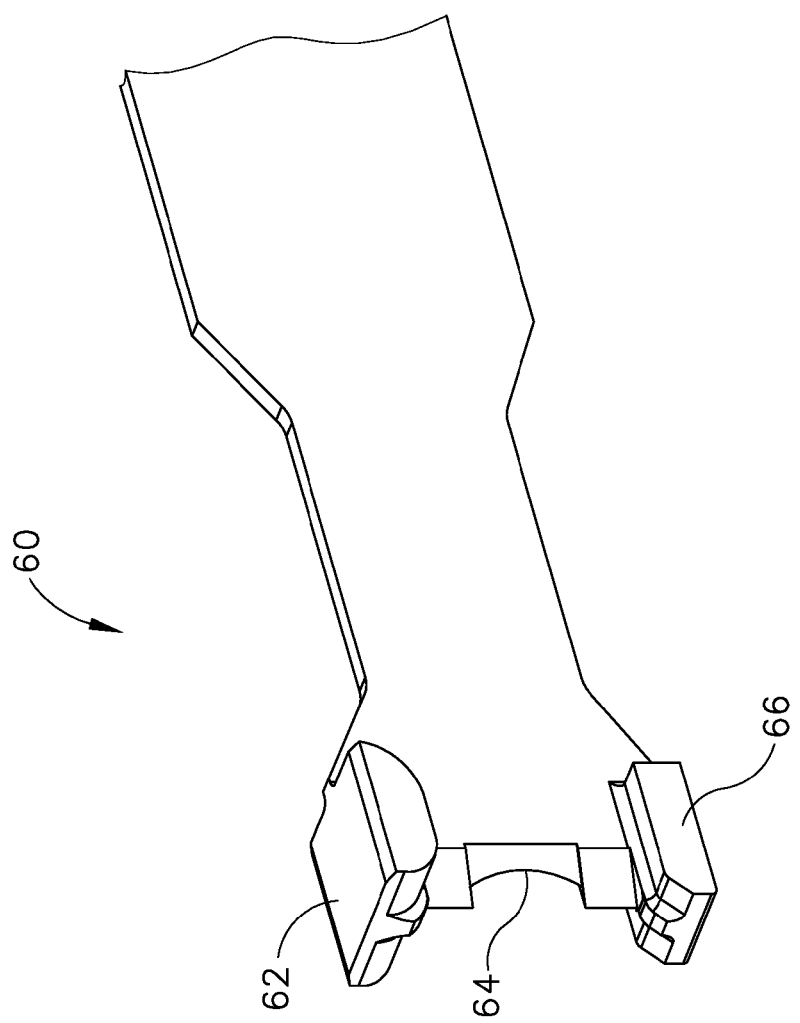
FIG. 5 depicts a partial perspective view of the distal end of the firing beam of the end effector of FIG. 2.

As also seen in FIGS. 2-5, electrosurgical instrument (10) of the present example includes a firing beam (60) that is longitudinally movable along part of the length of end effector (40). Firing beam (60) is coaxially positioned within shaft (30), extends along the length of shaft (30), and translates longitudinally within shaft (30) (including articulation section (36) in the present example), though it should be understood that firing beam (60) and shaft (30) may have any other suitable relationship. In some versions, a proximal end of firing beam (60) is secured to a firing tube or other structure within shaft (30); and the firing tube or other structure extends through the remainder of shaft (30) to handpiece (20) where it is driven by movement of trigger (24). As best seen in FIG. 5, firing beam (60) includes a sharp distal blade (64), an upper flange (62), and a lower flange (66). As best seen in FIG. 4, distal blade (64) extends through slots (46, 48) of jaws (42, 44), with upper flange (62) being located above jaw (44) in recess (59) and lower flange (66) being located below jaw (42) in recess (58). The configuration of distal blade (64) and flanges (62, 66) provides an "I-beam" type of cross section at the distal end of firing beam (60). While flanges (62, 66) extend longitudinally only along a small portion of the length of firing beam (60) in the present example, it should be understood that flanges (62, 66) may extend longitudinally along any suitable length of firing beam (60). In addition, while flanges (62, 66) are positioned along the exterior of jaws (42, 44), flanges (62, 66) may alternatively be disposed in corresponding slots formed within jaws (42, 44). For instance, each jaw (42, 44) may define a "T"-shaped slot, with parts of distal blade (64) being disposed in one vertical portion of each "T"-shaped slot and with flanges (62, 66) being disposed in the horizontal portions of the "T"-shaped slots. Various other suitable configurations and relationships will be apparent to those of ordinary skill in the art in view of the teachings herein.

Distal blade (64) is substantially sharp, such that distal blade (64) will readily sever tissue that is captured between jaws (42, 44). Distal blade (64) is also electrically grounded in the present example, providing a return path for RF energy as described elsewhere herein. In some other versions, distal blade (64) serves as an active electrode.

The "I-beam" type of configuration of firing beam (60) provides closure of jaws (42, 44) as firing beam (60) is advanced distally. In particular, flange (62) urges jaw (44) pivotally toward jaw (42) as firing beam (60) is advanced from a proximal position (FIGS. 1-3) to a distal position (FIG. 4), by bearing against recess (59) formed in jaw (44).

This closing effect on jaws (42, 44) by firing beam (60) may occur before distal blade (64) reaches tissue captured between jaws (42, 44). Such staging of encounters by firing beam (60) may reduce the force required to squeeze trigger (24) to actuate firing beam (60) through a full firing stroke. In other words, in some such versions, firing beam (60) may have already overcome an initial resistance required to substantially close jaws (42, 44) on tissue before encountering resistance from severing the tissue captured between jaws (42, 44). Of course, any other suitable staging may be provided.

In the present example, flange (62) is configured to cam against a ramp feature at the proximal end of jaw (44) to open jaw (44) when firing beam (60) is retracted to a proximal position and to hold jaw (44) open when firing beam (60) remains at the proximal position. This camming capability may facilitate use of end effector (40) to separate layers of tissue, to perform blunt dissections, etc., by forcing jaws (42, 44) apart from a closed position. In some other versions, jaws (42, 44) are resiliently biased to an open position by a spring or other type of resilient feature. While jaws (42, 44) close or open as firing beam (60) is translated in the present example, it should be understood that other versions may provide independent movement of jaws (42, 44) and firing beam (60). By way of example only, one or more cables, rods, beams, or other features may extend through shaft (30) to selectively actuate jaws (42, 44) independently of firing beam (60). Such jaw (42, 44) actuation features may be separately controlled by a dedicated feature of handpiece (20). Alternatively, such jaw actuation features may be controlled by trigger (24) in addition to having trigger (24) control firing beam (60). It should also be understood that firing beam (60) may be resiliently biased to a proximal position, such that firing beam (60) retracts proximally when a user relaxes their grip on trigger (24).

In some variations, firing beam (60) is modified such that flanges (62, 66) are replaced with pins that extend transversely from the modified firing beam. In other words, one or more upper pins could bear against recess (59) of jaw (44), and one or more lower pins could bear against recess (58) of jaw (42), as the modified firing beam is advanced distally through slots (46, 48). In some such versions, one or more of the pins may be configured to rotate about axes that extend transversely from the modified firing beam, such that the pins roll along recesses (58, 59) as the modified firing beam translates longitudinally through slots (46, 48). The pins may thus provide reduced friction with jaws (42, 44), thereby reducing the force required to translate the modified firing beam. In addition or in the alternative, at least one of the pins may be slidably disposed in a corresponding elongate slot formed through the modified firing beam, such that the pin may translate along a plane defined by the modified firing beam. By way of example only, a modified firing beam may be configured in accordance with at least some of the teachings of U.S. Pub. No. 2012/0083783, the disclosure of which is incorporated by reference herein. Other suitable ways in which firing beam (60) may be varied will be apparent to those of ordinary skill in the art in view of the teachings herein.

D. Exemplary Operation

In an exemplary use, end effector (40) is inserted into a patient via a trocar. Articulation section (36) is substantially straight when end effector (40) and part of shaft (30) are inserted through the trocar. The articulation control, if equipped, may then be manipulated to pivot or flex articulation section (36) of shaft (30) in order to position end effector (40) at a desired position and orientation relative to an anatomical structure within the patient. Two layers of tissue of the anatomical structure are then captured between jaws (42, 44) by squeezing trigger (24) toward pistol grip (22). Such layers of tissue may be part of the same natural lumen defining anatomical structure (e.g., blood vessel, portion of gastrointestinal tract, portion of reproductive system, etc.) in a patient. For instance, one tissue layer may comprise the top portion of a blood vessel while the other tissue layer may comprise the bottom portion of the blood vessel, along the same region of length of the blood vessel (e.g., such that the fluid path through the blood vessel before use of electrosurgical instrument (10) is perpendicular to the longitudinal axis defined by end effector (40), etc.). In other words, the lengths of jaws (42, 44) may be oriented perpendicular to (or at least generally transverse to) the length of the blood vessel. As noted above, flanges (62, 66) cammingly act to pivot jaw (44) toward jaw (42) when firing beam (60) is actuated distally by squeezing trigger (24) toward pistol grip (22). Jaws (42, 44) may be substantially clamping tissue before trigger (24) has swept through a full range of motion toward pistol grip (22), such that trigger (24) may continue pivoting toward pistol grip (22) through a subsequent range of motion after jaws (42, 44) have substantially clamped on the tissue.

With tissue layers captured between jaws (42, 44) firing beam (60) continues to advance distally by the user squeezing trigger (24) further toward pistol grip (22). As firing beam (60) continues to advance distally, distal blade (64) simultaneously severs the clamped tissue layers, resulting in separated upper layer portions being apposed with respective separated lower layer portions. In some versions, this results in a blood vessel being cut in a direction that is generally transverse to the length of the blood vessel. It should be understood that the presence of flanges (62, 66) immediately above and below jaws (42, 44), respectively, help keep jaws (42, 44) in a closed and tightly clamping position. In particular, flanges (62, 66) help maintain a significantly compressive force between jaws (42, 44). With severed tissue layer portions being compressed between jaws (42, 44), bipolar RF energy is applied to the tissue through electrodes (50, 52) by the user depressing activation button (26). Thus, a bipolar RF current flows through the compressed regions of severed tissue layer portions. The bipolar RF energy delivered by power source (80) ultimately thermally welds the tissue layer portions on one side of firing beam (60) together and the tissue layer portions on the other side of firing beam (60) together.

In certain circumstances, the heat generated by activated electrodes (50, 52) can denature the collagen within the tissue layer portions and, in cooperation with clamping pressure provided by jaws (42, 44), the denatured collagen can form a seal within the tissue layer portions. Thus, the severed ends of the natural lumen defining anatomical structure are hemostatically sealed shut, such that the severed ends will not leak bodily fluids. In some versions, electrodes (50, 52) may be activated with bipolar RF energy before firing beam (60) even begins to translate distally and thus before the tissue is even severed. For instance, such timing may be provided in versions where button (26) serves as a mechanical lockout relative to trigger (24) in addition to serving as a switch between power source (80) and electrodes (50, 52). Other suitable ways in which instrument (10) may be operable and operated will be apparent to those of ordinary skill in the art in view of the teachings herein.

II. Exemplary Surgical Instrument with Hyperextendable Jaw

In some instances, it may be desirable to clean instrument (10) after instrument (10) has been used in a surgical procedure. For instance, it may be desirable to clean and sterilize a used instrument (10) in order to enable instrument (10) to be reused in a subsequent surgical procedure. However, the small size of jaws (42, 44) and other components may make it difficult to access certain parts of instrument (10) in order to effectively clean instrument (10) for reuse. It may therefore be desirable to modify instrument (10) in order to facilitate cleaning and sterilization of instrument (10). Merely illustrative examples of modifications that may be made to instrument (10) in order to facilitate cleaning and sterilization of instrument (10) will be described in greater detail below, while further variations will be apparent to those of ordinary skill in the art in view of the teachings herein.

FIGS. 6A-7C show one merely exemplary variation of an electrosurgical instrument (100) having features that enable cleaning of the end effector (140) and other portions of instrument (100). It should be understood that, in many respects, instrument (100) is configured and operable substantially similar to instrument (10) described above, except for the differences discussed below. Electrosurgical instrument (100) of the present example includes a handpiece (120), a shaft (130) extending distally from handpiece (120), and an end effector (140) disposed at a distal end of shaft (30). Handpiece (120) of the present example includes a pistol grip (122), a pivoting trigger (124), an activation button (126), and a knob (134) that is operable to rotate shaft (130) relative to handpiece (120). Trigger (124) is pivotable toward and away from pistol grip (122) to selectively actuate end effector (140) as will be described in greater detail below. In that regard, end effector (140) of the present example functions substantially similar to end effector (40) described above except for the differences discussed below. In particular, end effector (140) may be used to capture tissue, apply RF energy to the captured tissue to seal the captured tissue, and sever the captured tissue after or during the sealing of the tissue in a substantially similar manner as described above.

Trigger (124) and activation button (126) are configured to operate substantially similar to trigger (24) and activation button (26), respectively, except for the differences discussed below. For instance, trigger (124) is pivotable toward and away from a pistol grip (122) to selectively actuate jaws (142, 144). In the example shown, end effector (140) is actuatable between an open configuration (FIGS. 6A, 7A) and a closed configuration (FIGS. 6C, 7C). As shown, trigger (124) is in a home position when end effector (140) is in the open configuration; and in an inward position toward pistol grip (122) (FIG. 7C) when end effector is in the closed configuration.

Jaws (142, 144) may be actuated by firing beam (160) in a substantially similar manner to that described above with respect to jaws (42, 44) and firing beam (60, 70). On the other hand, by way of example only, one or more cables, rods, beams, or other features may extend through shaft (130) to selectively actuate jaws (142, 144) independently of firing beam (160). Such jaw (142, 144) actuation features may be separately controlled by a dedicated feature of handpiece (120). Alternatively, such jaw actuation features may be controlled by trigger (124) in addition to having trigger (124) controlling firing beam (160). It should also be understood that firing beam (160) may be resiliently biased toward a proximal position, such that firing beam (160) retracts proximally when a user relaxes their grip on trigger (124). In addition or in the alternative, jaw (144) may be resiliently biased toward the open position, such that jaw (144) opens when the user relaxes their grip on trigger (124).

Trigger (124) of the present example is further pivotable to an outward position (FIG. 6B) whereby the angle between trigger (124) and pistol grip (122) is greater than in the home position and the inward position. As trigger (124) is moved to the outward position, end effector (140) actuates to an extended open configuration (FIGS. 6B, 7B) that provides better access to the jaws (142, 144) for cleaning. In the present example, firing beam (160) also advances distally as trigger (124) is moved to the outward position, thereby also providing better access to firing beam (160) for cleaning. However, in other examples, the firing beam (160) may remain in its proximal position as trigger (124) is moved to the outward position and may be moved to a distal position for cleaning, for example, independent of the movement of jaws (142, 144). As shown, the angle between first jaw (142) and second jaw (144) is approximately 135 degrees when end effector (140) is in the open extended configuration. The angle between the first and second jaws (142, 144) when end effector (140) is in the extended open configuration may be between approximately 90 degrees and approximately 180 degrees. The angle between the first and second jaws (142, 144) may be taken from a point of reference on each of the first and second jaws (142, 144). In one example, first jaw (142) extends along a first axis (170) and the second jaw (144) extends along a second axis (172) that intersects the pivot point (176) about which the second jaw (144) pivots relative to the first jaw (142). In that example, the angle between the first and second jaws (142, 144) may be the angle between the first and second axes (170, 172). Of course, other reference points to measure the angle between jaws (142, 144) may be used.

Trigger (124) may be moved between the home and inward positions to move end effector (140) between the open and closed configurations, respectively, during and after use of instrument (100), while trigger (124) may be pivoted to the outward position to move end effector to the extended open configuration after use of the instrument (100), for cleaning. However, in some circumstances, it may be necessary or desired to pivot trigger (124) to the outward position during use of instrument (100) in order to move end effector (140) to the open extended configuration.

In at least one example, trigger (124) is biased toward the home position when trigger (124) is in the inward position (and end effector (140) is in the closed configuration). In some versions of this example, once the user relaxes their grip from trigger (124), trigger (124) will be urged toward the home position, thus also moving the end effector (140) to the open configuration. However, in some other examples, trigger (124) is not biased toward the home position when in the inward position. Regardless of whether trigger (124) is biased toward the home position from the inward position, trigger (124) may be biased towards the home position when trigger (124) is in the outward position (and end effector (140) is in the extended open configuration). Alternatively, trigger (124) may not be biased toward the home position from the outward position in some other versions. Moreover, in some examples, and as described in more detail below, trigger (124) may be lockable in the outward position to thereby lock the end effector (140) in the extended open configuration, which may simplify the cleaning process of end effector (140). In versions where trigger (124) is biased toward the home position from the inward position and/or from the outward position, various kinds of components may be used to provide such bias(es). By way of example only, such resilient bias may be provided by one or more torsion springs, one or more coil springs, one or more leaf springs, and/or any other suitable kind(s) of resilient member(s).

Figure 6A:
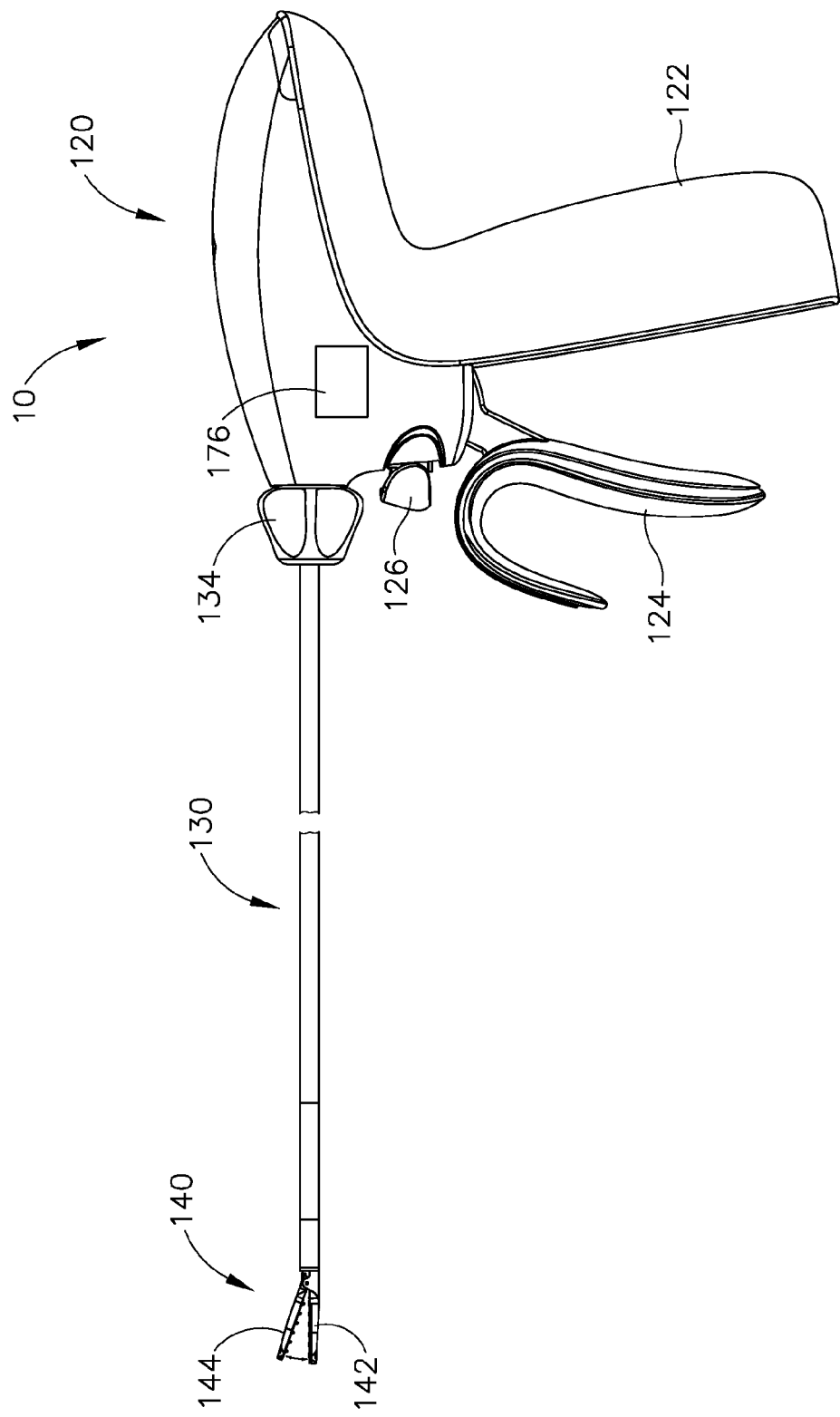
FIG. 6A depicts a side elevational view of an exemplary alternative medical instrument, showing an end effector of the instrument in an open configuration.
Figure 6C:
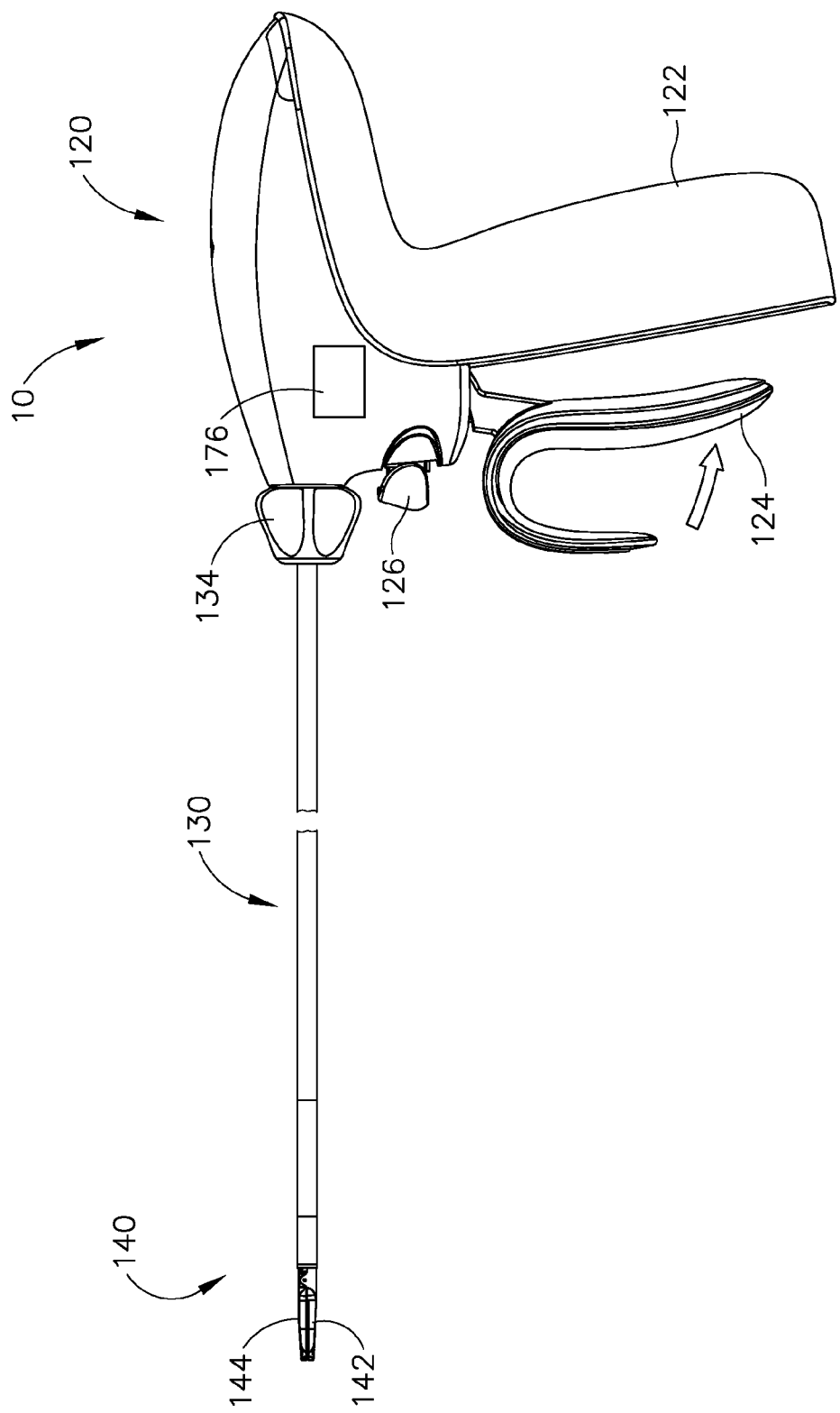
FIG. 6C depicts a side elevational view of the instrument of FIG. 6A, showing the end effector in a closed configuration.

The relative positions of the trigger (124) among the various positions are not limited to those shown in FIGS. 6A-C. Moreover, the positions of trigger (124) associated with particular configurations of the end effector (140) are not limited to those shown in FIGS. 6A-C. Further, instrument (100) may be configured to operate such that the operative relationship is essentially opposite as described above; that is, in one example, the extended open configuration of end effector (140) may be associated with the inward position of trigger (124), while the closed configuration of end effector (140) may be associated with an outward position of trigger (124).

In the example shown, instrument (100) includes a switch (176) that is switchable between locked and unlocked states. When in the locked state, switch (176) prevents trigger (124) from pivoting away from pistol grip (122) past the home position to the outward position and therefore limits the path of travel of second jaw (144) relative to first jaw (142). Particularly, when switch (176) of the present example is in the locked state, trigger (124) is still able to travel between the inward and home positions, thus allowing pivoting of second jaw (144) relative to first jaw (142) through a first range of angular movement. The first range of angular movement is between a minimum angle and a first maximum angle, such that the minimum angle and the first maximum angle serve as lower and upper bounds, respectively. In the present example, second jaw (144) is capable of achieving an angle of approximately zero degrees relative to first jaw (142), such that the first range of angular movement has a lower bound of approximately zero degrees as a minimum angle. However, it should be understood that the first range of angular movement may instead be bound by any other suitable minimum angle. Also in the present example, when switch (176) is in the locked state, the first maximum angle between the first jaw (142) and second jaw (144) may be between twenty five degrees and sixty degrees. In some versions, when switch (176) is in the locked state, the first maximum angle between the first jaw (142) and second jaw (144) is between thirty five degrees and sixty degrees. Alternatively, any other suitable first maximum angle may be provided. It should be understood that the first maximum angle of second jaw (144) relative to first jaw (142) is associated with the home position of trigger (124), such that when trigger (124) is in the home position, second jaw (144) is disposed at the first maximum angle relative to first jaw (142).

Figure 7A:
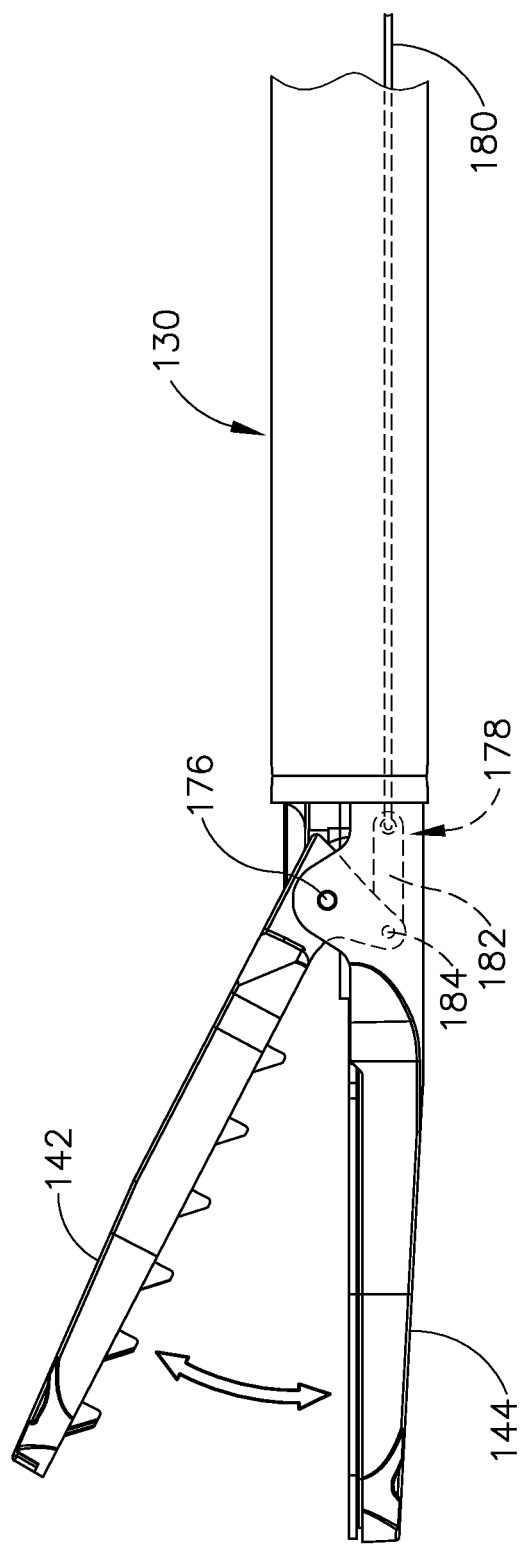
FIG. 7A depicts a detailed side elevational view of the end effector of FIG. 6A, showing the end effector in the open configuration.

When second jaw (144) is oriented relative to first jaw (142) at an angle that is greater than approximately zero degrees and less than or equal to first maximum angle, end effector (140) may be referred to as being in the open configuration (e.g., FIG. 7A). Similarly, when second jaw (144) is oriented at an angle of approximately zero degrees relative to first jaw (142), end effector (140) may be referred to as being in the closed configuration (e.g., FIG. 7C). It should be understood that, in some instances, the properties of tissue (e.g., thickness, density, etc.) between jaws (142, 144) may prevent second jaw (144) from actually reaching an angle of zero degrees relative to first jaw (142). In such instances, end effector (140) may still be considered as being at a closed configuration when second jaw (144) is compressing the tissue against first jaw (142).

Figure 7B:
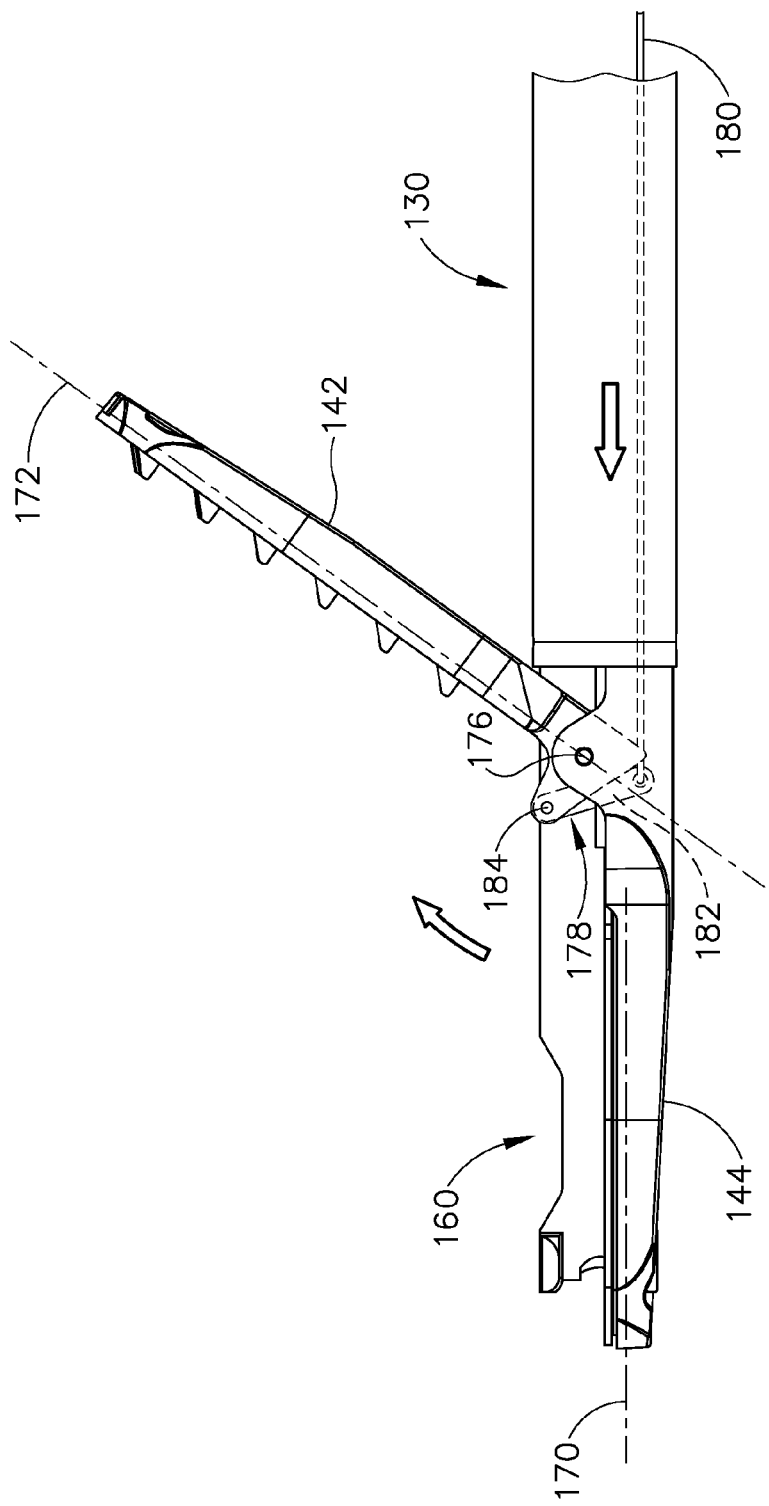
FIG. 7B depicts a detailed side elevational view of the end effector of FIG. 6A, showing the end effector in the extended open configuration.
Figure 7C:
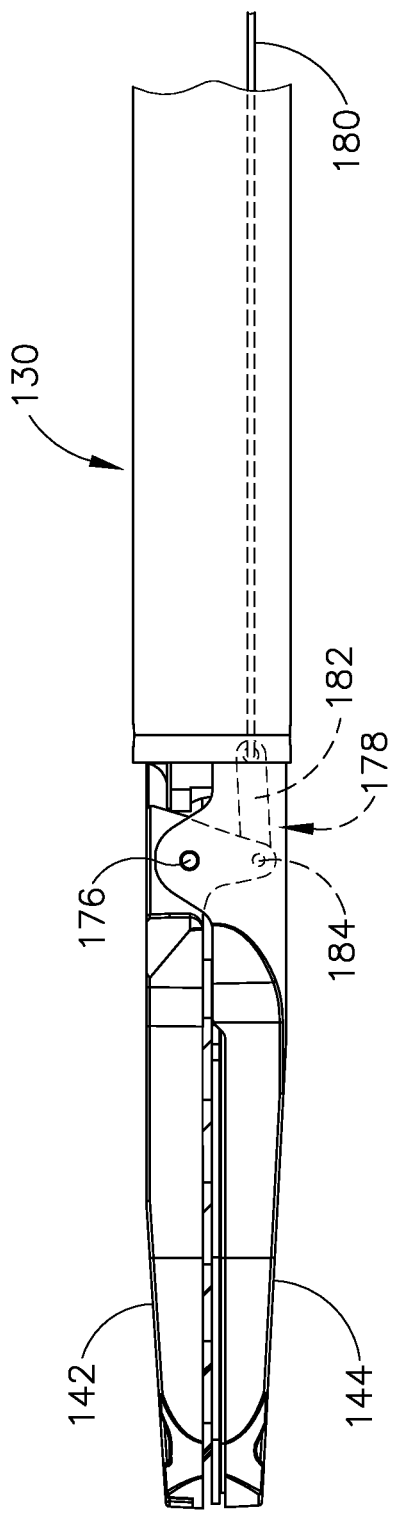
FIG. 7C depicts a detailed side elevational view of the end effector of FIG. 6A, showing the end effector in the closed configuration.

When switch (176) of the present example is transitioned to the unlocked state, trigger (124) is able to pivot away from pistol grip (122) past the home position. Therefore, when switch (176) is in the unlocked state, second jaw (144) is able to pivot further away from first jaw (142) such that the angle between the first and second jaws (142, 144) is greater than the first maximum angle. As shown in FIG. 7B, second jaw (144) is able to pivot through a second range of angular movement such that the angle between first and second jaws (142, 144) is moveable between the first maximum angle and a second maximum angle. The second maximum angle in the present example is between approximately ninety degrees and approximately 180 degrees. However, in other examples, the second maximum angle may be less than approximately ninety degrees or greater than approximately 180 degrees. In the example shown, the second maximum angle is associated with the outward position of trigger (124) such that when trigger (124) is in the outward position, second jaw (144) is disposed at the second maximum angle relative to first jaw (142). Moreover, the configuration of end effector (140) when second jaw (144) has pivoted past the first maximum angle may be referred to as an open extended configuration. Alternatively, the open extended configuration of end effector (140) may refer to a situation where second jaw (144) has reached the second maximum angle (e.g., FIG. 7C).

In at least one example, trigger (124) may be lockable in the outward position such that end effector (140) is lockable in the extended open configuration, to further facilitate cleaning of end effector (140). In such examples, switch (176) may be configured to transition to a second locked state to lock trigger (124) in the outward position such that end effector (140) is locked in the extended open configuration. For example, switch (176) may also serve as a mechanical lockout against trigger (124) such that trigger (124) cannot be pivoted inward toward the home position from the outward position until switch (176) is again actuated to unlock trigger (124) from the outward position.

Switch (176) may automatically transition to the second locked state when trigger (124) reaches the outward position or, alternatively, the user may need to affirmatively actuate switch (176) to the second locked state to lock trigger (124) in the outward position. In either version where trigger (124) is lockable in the outward position, the user may need to actuate switch (176) again in order to transition switch (176) to the unlocked state, thereby allowing trigger (124) to be pivoted back to the home position. Alternatively, switch (176) may be configured such that the second locked state may be overcome by the user pivoting trigger (124) towards pistol grip (122) with a sufficient amount of force to overcome the second locked state. In some examples, switch (176) may be configured to automatically transition to the first locked state once trigger (124) again reaches the home position. Alternatively, the user may need to affirmatively actuate switch (176) to the first locked state once trigger (124) reaches the home position. In either case, the user would need to subsequently actuate switch (176) again in order to pivot trigger (124) back to the outward position again after returning to the home position. Still other suitable operabilities that may be provided in association with switch (176) will be apparent to those of ordinary skill in the art in view of the teachings herein.

As shown, switch (176) is positioned on a left side of handpiece (120). In some such versions, switch (176) may be actuated with the thumb of the hand that is grasping pistol grip (122). However, the position of the switch (176) is not so limited and switch (176) may be positioned on other parts of handpiece (120) or instrument (100). Switch (176) may take many forms and may include electrical, electronic, or mechanical components, or a combination thereof. In some versions, switch (176) may simply comprise a mechanically activated member that is movable to and from a position where switch (176) (or an arm or other component in communication with switch (176), for example) impedes or otherwise prevents the pivoting of trigger (124). In some other versions, switch (176) may comprise a button that, upon being pressed, activates an electronic component (e.g., solenoid) that moves a component to and from a position where switch (176) impedes or otherwise prevents the pivoting of trigger (124). Other suitable switch (176) configurations will be apparent to those of ordinary skill in the art in view of the teachings herein. Similarly, various structures and components that may be coupled with switch (176) in order to provide the operabilities described herein will be apparent to those of ordinary skill in the art in view of the teachings herein.

Moreover, although one switch (176) is shown, instrument (100) may include more than one switch (176). For example, instrument (100) may include two switches, where a first one of the switches is associated with the locked state of switch (176) that prevents trigger (124) from pivoting outwardly to the outward position from the home position; and a second one of the switches is associated with the second locked state that locks trigger (124) in the outward position. In still other examples, instrument (100) may not have a switch (176) or other locking mechanism that locks trigger in one or more positions. In some such examples, instrument (100) may include biasing elements or other members that operate to maintain trigger (124) in certain positions unless certain forces or pressures are applied to trigger (124).

In the example shown, and as best seen in FIGS. 7A-7C, instrument (100) includes a linkage system (178) that operably couples the trigger (124) and the end effector (140). Particularly, linkage system (178) operably couples second jaw (144) and trigger (124) such that pivoting trigger (124) results in actuation of the second jaw (144) relative to the first jaw (142) as described above. Linkage system (178) comprises an elongate member (180), which is operable to translate longitudinally within shaft (130). By way of example only, elongate member (180) may comprise a push-pull cable, a rod, a band, a beam, a tubular member, and/or any other suitable structure(s). A proximal end of elongate member (180) is coupled with trigger (124), such that pivotal movement of trigger (124) toward pistol grip (122) causes proximal movement of elongate member (180) in shaft (130); and such that pivotal movement of trigger (124) away from pistol grip (122) causes distal movement of elongate member (180) in shaft (130). Various suitable features and structures that may be used to couple trigger (124) with elongate member (180) to provide such operability will be apparent to those of ordinary skill in the art in view of the teachings herein. A distal end of elongate member (180) is pivotably coupled to a first end of a link (182). A second end of link (182) is pivotably coupled to a first pin hole (184) of second jaw (144). Second jaw (144) is also pivotably coupled to shaft (130) at pivot point (176) such that second jaw (144) is pivotable relative to shaft (130) about pivot point (176).

In operation, as elongate member (180) is advanced distally from the position shown in FIG. 7A to the position shown in FIG. 7B, elongate member (180) urges link (182) in the distal direction. Link (182) urges the end of second jaw (144) at first pin hole (184) distally, causing the pivoting of second jaw (144) about pivot point (176) from the position shown in FIGS. 6A and 7A to the position shown in FIGS. 6B and 7B. As described above, second jaw (144) may or may not be locked in the open extended configuration shown in FIGS. 6B and 7B at this stage. As elongate member (180) is retracted proximally from the position shown in FIG. 7A, elongate member (180) urges link (182) in the proximal direction. Link (182) urges the end of second jaw (144) at first pin hole (184) proximally, causing the pivoting of second jaw (144) about pivot point (176) from the position shown in FIGS. 6A and 7A to the position shown in FIGS. 6C and 7C. It will be understood that although only one linkage system (178) is shown, two linkage systems may be provided such that individual linkage systems each may coupled to an opposite side of the second jaw (144) not visible in the figures.

III. Exemplary Surgical Instrument with Flush Port in Shaft

Ingress of fluid, tissue, and other materials into areas of an instrument (10, 100) may cause various issues. For example, fluids and tissue may be difficult to remove from certain components of instrument (10, 100) (e.g., shaft (30, 130) and other internal components that are proximal to end effector (40, 140)) during a cleaning and sterilization process after use of instrument (10, 100). Moreover, ingress of fluids up the shaft (30, 130) and into portions of instrument (10, 100) may occur during use. For instance, fluid ingress up the shaft (30, 130) may be influenced by the pressure differential created by insufflation during a laparoscopic procedure. This pressure differential may essentially force fluid up the shaft (30, 130) and into the instrument body, such as handpiece (20, 120), potentially resulting in damage to unprotected electronics. Moreover, once fluid reaches the handpiece (20, 120), fluids may leak out of handpiece (20, 120). In addition to potentially damaging the instrument (10, 100), fluids and other material that migrate into the shaft (30, 130) may make it difficult to clean shaft (30, 130) and other parts of instrument (10, 100). It may therefore be desirable to provide features that restrict or prevent ingress of fluids into interior regions of instrument (10, 100) and/or that facilitate cleaning of interior regions of instrument (10, 100).

Figure 8:
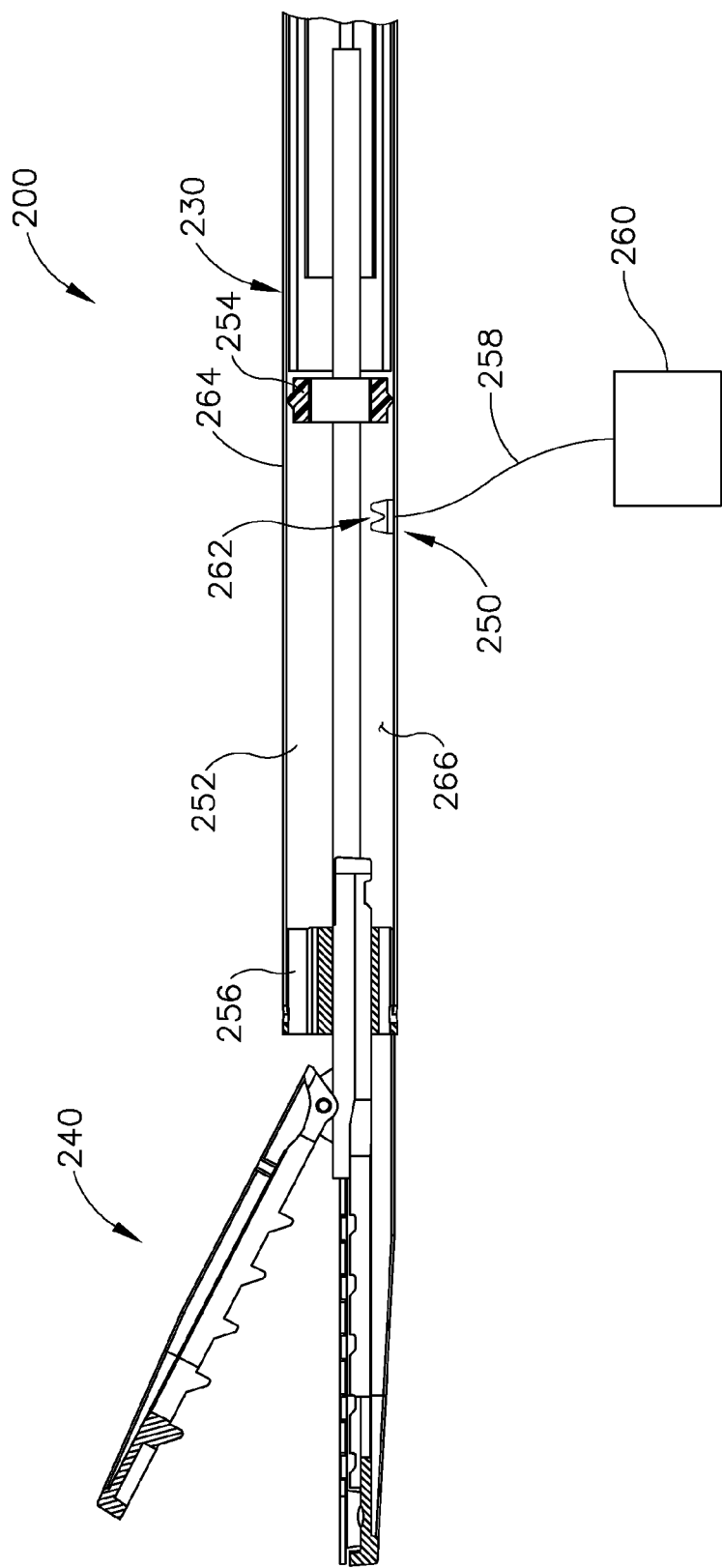
FIG. 8 depicts a cross-sectional side view of the distal end of a shaft assembly of an exemplary alternative medical instrument with an end effector in an open configuration.
Figure 9:
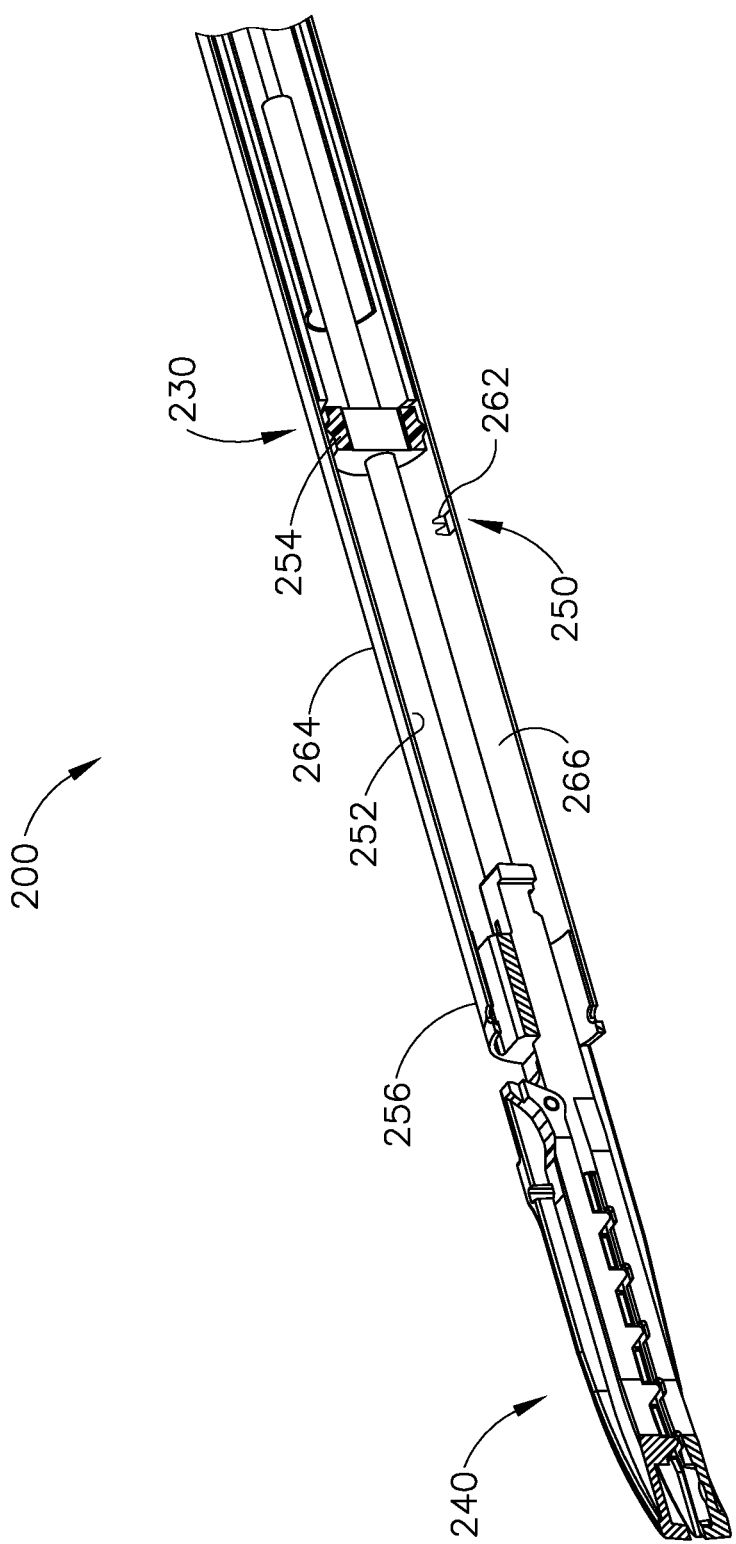
FIG. 9 depicts a cross-sectional perspective view of the distal end of the shaft assembly of FIG. 8, but with the end effector in a closed configuration.

FIGS. 8-9 show a distal end of an exemplary alternative shaft assembly (230) having features that provide for cleaning of internal components and that, additionally or alternatively, prevent ingress of fluids up the shaft (230). It should be understood that shaft assembly (230) may be readily incorporated into instrument (10, 100) described above except for the differences discussed below. An end effector (240) is positioned at the distal end of shaft (230). End effector (240) of the present example functions substantially similar to end effector (40, 140) described above except for the differences discussed below. In particular, end effector (240) may be used to capture tissue, apply RF energy to the captured tissue to seal the captured tissue, and sever the captured tissue after or during the sealing of the tissue in a substantially similar manner as described above. It will be further understood that instrument (200) includes many identical or substantially similar components as instrument (10, 100). However, FIGS. 8-9 do not depict certain components present in instrument (10, 100), as at least some of those components have been hidden for clarity.

In the example shown, shaft (230) includes a port (250) that enables fluid to be directed into a lumen (252) of shaft (230) in order to clean lumen (252) and other internal components of instrument. The port (250) may be fluidly coupled to a source of fluid, such as pressurized enzymatic fluid, as described in more detail below. As shown, the port (250) is disposed on the shaft (230) between the end effector (240) and an O-ring (254) that substantially seals off the distal end (256) of the shaft (230) from the rest of the instrument (200). Although in some circumstances the O-ring (254) may completely seal off the distal end (256) of shaft (230) such that it prevents any fluid from traveling into proximal portions of shaft (230), in other circumstances a small amount of fluid may pass by the O-ring (254) or other adjacent structures such that O-ring (254) still substantially seals off the distal end (256) of shaft (230). Of course, the position of the O-ring (254) relative to the end effector (240), and the relative position of the port (250) between the end effector (240) and the O-ring (254), may be different than those positions shown. Moreover, the position of the port (250) may be varied along, and about, a longitudinal axis defined by shaft (230). While only one port (250) is shown, in alternative examples, shaft (230) may comprise more than one port (250).

In the example shown, port (250) is configured to receive a conduit (258) from a source (260) of fluid. In one example, port (250) is configured such that the conduit (258) may snap into the port (250). In that regard, port (250) and conduit (258) may include correspondingly fitting male and female parts. In the example shown, the port (250) includes a female portion to receive the male portion of the conduit (258). One or both of the port (250) and the conduit (258) may include resilient features that enable the snap fitting of the port (250) and the conduit (258) relative to one another. Further, in some examples, one or both of the port (250) and conduit (258) may include a nozzle configured to direct a pressurized flow of fluid into lumen (252). Various other manners of coupling the port (250) to the conduit (258) will be apparent to those of ordinary skill in the art in view of the teachings herein. In at least one example, however, the port (250) and the conduit (258) need not be fixedly coupled together. Rather, in at least one example, the port (250) and the conduit (258) may simply be placed in fluid communication with one another and each held by one or more users such that fluid may be directed from conduit (258) into lumen (252). As shown in FIGS. 8-9, port (250) further comprises a valve seal (262) that substantially prevents fluid from exiting out of port (250). The valve seal (262) may be in the form of a duckbill or other seal, and may comprise an elastomeric material and/or other suitable material. Various other seal designs will be apparent to those of ordinary skill in the art in view of the teachings herein.

As shown, the port (250) is configured such that the port (250) does not substantially interfere with the instrument (200) being inserted into or removed from a trocar, for example, in instances where instrument (200) is used in an endoscopic or laparoscopic setting. For example, an outermost portion of the port (250) may be positioned to be substantially flush with an outer wall (264) of shaft (230). Therefore, in such examples, the port (250) should not significantly increase friction between shaft (230) and a trocar, for example.

In use, the port (250) is fluidly coupled to source (260) of fluid (e.g., an enzymatic cleaner under pressure), such as via conduit (258) described above, after the instrument has been used. In some versions, the fluid may be an enzymatic cleaner such as Cydex, but is not so limited. The fluid may then be directed through the conduit (258) into lumen (252) at a pressure that is sufficient to clean tissue, coagulated blood, and/or other debris from the lumen (252), as well as from other internal components, driving the debris distally. In some versions, all or some portions of end effector (240), and other components such as the firing beam (e.g., firing beam (60) in FIG. 4, firing beam (70) in FIG. 5) may optionally be disassembled or removed from instrument (200) to enable the fluid and debris such as tissue to flow out from the distal end (256) of shaft (230) as the fluid is directed into lumen (252). However, instrument (200) need not necessarily be disassembled in order to be cleaned and sanitized. Once cleaned and optionally sanitized with the fluid, conduit (258) may be decoupled from port (250). In some examples, instrument (200) may be subjected to additional cleaning. If instrument (200) was disassembled fully or partially, instrument (200) may be reassembled. Instrument (200) may be subjected to a sterilization process after being cleaned with the fluid. For example, instrument (200) may be placed in a closed and sealed container, such as a plastic or TYVEK bag. Instrument (200) may then be placed in a field of radiation that can penetrate the container, such as gamma radiation, x-rays, or high-energy electrons. The radiation may kill bacteria on instrument (200) and in the container. The sterilized instrument (200) may then be stored in the sterile container for later use. Instrument (200) may also be sterilized using any other technique known in the art, including but not limited to beta or gamma radiation, ethylene oxide, or steam, and need not necessarily be placed into a container before a sterilization process.

In addition or in the alternative, port (250) may be utilized during use of the instrument in a surgical procedure. For example, port (250) may be coupled to a source of saline, for example, such that a supply of saline may be directed into lumen (252) during use of the instrument to prevent the ingress of blood, tissue, and other debris into shaft (230). In some such versions, the pressure of the fluid within lumen (252) and/or the outward flow of fluid from lumen (252) is sufficient to prevent a substantial ingress of blood, tissue, and other debris into lumen (252). Therefore, the cleaning and sanitizing process after use of instrument (200) may potentially be obviated or negated to a certain extent, at least with respect to lumen (252) and other internal components. In some uses, port (260) is used to flush debris from shaft (230) in the middle of a surgical procedure after shaft (230) has been removed from the patient. Shaft (230) is then reinserted in the patient to perform additional steps in the same surgical procedure. Other suitable ways in which port (250) may be used will be apparent to those of ordinary skill in the art in view of the teachings herein.

In some versions, one or more components/features of shaft (30, 130, 230) comprises a superhydrophobic material. The shaft (30, 130, 230) itself may be made from a superhydrophobic material. Alternatively, all or only certain portions of the shaft (30, 130, 230) may be coated with a superhydrophobic material. In the example shown in FIGS. 8-9, inner wall (266) of shaft (230) that defines lumen (252) that is coated with a superhydrophobic material. It should also be understood that one or more portions of handpiece (20, 120) may be coated with (or be otherwise provided with) a superhydrophobic material.

"Superhydrophobic," as used herein, is meant to refer to a material that provides a contact angle of greater than ninety degrees between one or more components/features of shaft (30, 130, 230) and a liquid and/or a contact angle of greater than ninety degrees between one or more components/features of handpiece (20, 120) and a liquid, whether the liquid is blood, saline, another liquid, or a mixture thereof. A contact angle of greater than ninety degrees may reduce the adherence of such liquids. This may further reduce the migration of fluids that might otherwise occur along the length of shaft (30, 130, 230) toward handpiece (20, 120) through capillary action. It should be understood that, when surfaces that define a small channel or conduit are coated with a superhydrophobic material, the superhydrophobic material may effectively provide a seal of the small channel or conduit such that the superhydrophobic material prevents the passage of fluid through the small channel or conduit.

Some exemplary superhydrophobic materials that may be utilized as the superhydrophobic material described above include any superhydrophobic coating, manufactured by Sandia National Laboratory (Albuquerque, N. Mex., USA), with a contact angle of approximately 172 degrees; any nanotechnology superhydrophobic coating manufactured by Ross Technology Corporation (Leola, Pa., USA); Never-Wet®, manufactured by Rust-Oleum Corporation (Vernon Hills, Ill., USA), with a contact angle of greater than approximately 150 degrees; Superhydrophobic Antifouling Coating manufactured by Gelwell Biotech Corporation (Taiwan); Fluorothane, manufactured by Cytonix Corporation (Beltsville, Md., USA), with a contact angle of approximately 140 degrees; and Thermablock, manufactured by Microphase Coatings, Inc. (Garner, N.C., USA). Other suitable materials will be apparent to those of ordinary skill in the art in view of the teachings herein.

IV. Miscellaneous

It should be understood that any of the versions of electrosurgical instrument (10) described herein may include various other features in addition to or in lieu of those described above. By way of example only, any of the devices herein may also include one or more of the various features disclosed in any of the various references that are incorporated by reference herein.

It should also be understood that any of the devices described herein may be modified to include a motor or other electrically powered device to drive an otherwise manually moved component. Various examples of such modifications are described in U.S. Pub. No. 2012/0116379, entitled "Motor Driven Electrosurgical Device with Mechanical and Electrical Feedback," published May 10, 2012, now U.S. Pat. No. 9,161,803, issued Oct. 20, 2015, the disclosure of which is incorporated by reference herein. Various other suitable ways in which a motor or other electrically powered device may be incorporated into any of the devices herein will be apparent to those of ordinary skill in the art in view of the teachings herein.

It should also be understood that any of the devices described herein may be modified to contain most, if not all, of the required components within the medical device itself. More specifically, the devices described herein may be adapted to use an internal or attachable power source instead of requiring the device to be plugged into an external power source by a cable. Various examples of how medical devices may be adapted to include a portable power source are disclosed in U.S. Provisional Application Ser. No. 61/410,603, filed Nov. 5, 2010, entitled "Energy-Based Surgical Instruments," the disclosure of which is incorporated by reference herein. Various other suitable ways in which a power source may be incorporated into any of the devices herein will be apparent to those of ordinary skill in the art in view of the teachings herein.

While the examples herein are described mainly in the context of electrosurgical instruments, it should be understood that various teachings herein may be readily applied to a variety of other types of devices. By way of example only, the various teachings herein may be readily applied to other types of electrosurgical instruments, tissue graspers, tissue retrieval pouch deploying instruments, surgical staplers, surgical clip appliers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

In versions where the teachings herein are applied to a surgical stapling instrument, it should be understood that the teachings herein may be combined with the teachings of one or more of the following, the disclosures of all of which are incorporated by reference herein: U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," published Apr. 2, 2013; and U.S. Pat. No. 8,453,914, entitled "Motor-Driven Surgical Cutting Instrument with Electric Actuator Directional Control Assembly," published Jun. 4, 2013. Other suitable ways in which the teachings herein may be applied to a surgical stapling instrument will be apparent to those of ordinary skill in the art in view of the teachings herein.

In versions where the teachings herein are applied to an ultrasonic surgical instrument, it should be understood that some such instruments may lack a translating firing beam. The components described herein for translating a firing beam may instead simply translate a jaw closing member. Alternatively, such translating features may simply be omitted. In any case, it should be understood that the teachings herein may be combined with the teachings of one or more of the following: U.S. Pat. Pub. No. 2006/0079874, entitled "Tissue Pad for Use with an Ultrasonic Surgical Instrument," published Apr. 13, 2006, now abandoned, the disclosure of which is incorporated by reference herein; U.S. Pat. Pub. No. 2007/0191713, entitled "Ultrasonic Device for Cutting and Coagulating," published Aug. 16, 2007, now abandoned, the disclosure of which is incorporated by reference herein; U.S. Pat. Pub. No. 2007/0282333, entitled "Ultrasonic Waveguide and Blade," published Dec. 6, 2007, now abandoned, the disclosure of which is incorporated by reference herein; U.S. Pat. Pub. No. 2008/0200940, entitled "Ultrasonic Device for Cutting and Coagulating," published Aug. 21, 2008, the disclosure of which is incorporated by reference herein; U.S. Pat. No. 8,461,744, entitled "Rotating Transducer Mount for Ultrasonic Surgical Instruments," published Jun. 11, 2013, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; U.S. Pat. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein; and/or U.S. Pat. No. 6,783,524, entitled "Robotic Surgical Tool with Ultrasound Cauterizing and Cutting Instrument," issued Aug. 31, 2004, the disclosure of which is incorporated by reference herein. Other suitable ways in which the teachings herein may be applied to an ultrasonic surgical instrument will be apparent to those of ordinary skill in the art in view of the teachings herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for operating on tissue, the apparatus comprising:
   (a) a body;
   (b) an elongate shaft, wherein the elongate shaft extends distally from the body, wherein the elongate shaft comprises a distal end;
   (c) an end effector, wherein the end effector is disposed at the distal end of the elongate shaft, and wherein the end effector comprises:
      (i) a first jaw, wherein the first jaw extends parallel to the elongate shaft, and
      (ii) a second jaw, wherein the second jaw is selectively pivotable toward and away from the first jaw to capture tissue,
      wherein at least one of the first jaw or the second jaw is operable to apply RF energy to tissue; and
   (d) a locking mechanism, wherein the locking mechanism is configured to transition between a locked state and an unlocked state;
   wherein the locking mechanism in the locked state is configured to allow movement of the second jaw relative to the first jaw through a first range of angular movement, wherein the first range of angular movement of the second jaw is bound by a minimum angle and a first maximum angle relative to the first jaw, wherein the first maximum angle is greater than the minimum angle;

wherein the locking mechanism in the unlocked state is configured to allow movement of the second jaw relative to the first jaw through a second range of angular movement, wherein the second range of angular movement of the second jaw is bound by the first maximum angle and a second maximum angle relative to the first jaw, wherein the second maximum angle is greater than the first maximum angle, wherein the second maximum angle is obtuse; and wherein the first jaw is configured to maintain an orientation parallel to a longitudinal axis of the elongate shaft with the locking mechanism in the locked and unlocked states and as the second jaw moves through the first and second ranges of angular movement.

2. The apparatus of claim 1, wherein the second maximum angle is at least ninety degrees.

3. The apparatus of claim 1, wherein the second maximum angle is less than 180 degrees.

4. The apparatus of claim 1, wherein the first maximum angle is between twenty five degrees and sixty degrees.

5. The apparatus of claim 1, wherein the body comprises a handpiece having a trigger, wherein the trigger is operable to move the second jaw toward and away from the first jaw.

6. The apparatus of claim 5, wherein the locking mechanism is further in communication with the trigger, wherein the locking mechanism is operable to selectively prevent movement of the trigger.

7. The apparatus of claim 5, wherein the handpiece further comprises a grip member, wherein the second jaw is configured to pivot toward the first jaw in response to pivotal movement of the trigger toward the grip member, wherein the second jaw is configured to pivot away from the first jaw in response to pivotal movement of the trigger away from the grip member.

8. The apparatus of claim 5, wherein the trigger is movable relative to a grip member between a home position, an outward position, and an inward position, wherein the home position is associated with the first maximum angle, wherein the outward position is associated with the second maximum angle, wherein the inward position is associated with the minimum angle.

9. The apparatus of claim 8, wherein the trigger is movable in a first direction to reach the outward position from the home position, wherein the trigger is movable in a second direction to reach the inward position from the home position, wherein the first direction is opposite to the second direction.

10. The apparatus of claim 8, wherein the locking mechanism is configured to lock the trigger in the outward position.

11. The apparatus of claim 8, wherein the locking mechanism in the locked state is configured to selectively prevent movement of the trigger from the home position toward the outward position.

12. The apparatus of claim 1, wherein the locking mechanism is configured to transition to a second locked state when the second maximum angle is reached, wherein the locking mechanism in the second locked state is configured to maintain the second maximum angle between the first jaw and the second jaw in the second locked state.

13. The apparatus of claim 1, wherein at least a portion of the first jaw extends along a first axis, wherein at least a portion of the second jaw extends along a second axis, wherein the relative angle between the first jaw and the second jaw is defined by an angle between the first axis and the second axis.

14. An apparatus for operating on tissue, the apparatus comprising:
(a) a body;
(b) an elongate shaft, wherein the elongate shaft extends distally from the body, wherein the elongate shaft comprises a distal end;
(c) an end effector, wherein the end effector is disposed at the distal end of the elongate shaft, and wherein the end effector comprises:
(i) a first jaw, and
(ii) a second jaw, wherein the second jaw is selectively moveable in relation to the first jaw to capture tissue, wherein at least one of the first jaw or the second jaw is operable to apply RF energy to tissue; and
(d) a locking mechanism configured to transition between a locked state and an unlocked state, wherein the second jaw is configured to be moveable relative to the first jaw through a first range of angular movement when the locking mechanism is in the locked state, wherein the first range of angular movement of the second law is bound by a minimum angle and a first maximum angle defined between the first and second jaws;

wherein the second jaw is configured to be moveable relative to the first jaw through a second range of angular movement when the locking mechanism is in the unlocked state, wherein the second range of angular movement of the second jaw is bound by the first maximum angle and a second maximum angle defined between the first and second jaws, wherein the second maximum angle is greater than the first maximum angle; and wherein the first jaw is configured to extend parallel to the elongate shaft when the locking mechanism is in the locked and unlocked states and as the second jaw moves through the first and second ranges of angular movement.

15. The apparatus of claim 14, wherein the body comprises a trigger and a grip.

16. The apparatus of claim 15, wherein the trigger is moveable toward the grip from a neutral position to a proximal position when the locking mechanism is in the locked state, wherein the trigger is moveable away from the grip from the neutral position to a distal position when the locking mechanism is in the unlocked state.

17. An apparatus for operating on tissue, the apparatus comprising:
(a) a body;
(b) an elongate shaft that extends distally from the body, wherein the elongate shaft comprises a distal end;
(c) an end effector disposed at the distal end of the elongate shaft, wherein the end effector comprises a pivotable jaw and a fixed jaw, wherein the pivotable jaw is configured to pivot in relation to the fixed jaw, wherein the fixed jaw is fixed in relation to the elongate shaft, wherein at least one of the jaws is operable to apply RF energy to tissue; and
(d) a user input feature operable to transition between a locked state and an unlocked state, wherein the user input feature is configured to allow the pivotable jaw to selectively pivot relative to the fixed jaw through a first range of angular movement when in the locked state, wherein the first range of angular movement of the pivotable jaw is bound by a minimum angle and an intermediate angle relative to the fixed jaw such that the minimum angle and the intermediate angle of the pivotable jaw is defined between the pivotable and fixed jaws, wherein the intermediate angle is greater than the minimum angle, wherein the user input feature is configured to allow the pivotable jaw to selectively pivot relative to the fixed jaw through a second range of angular movement when in the unlocked state, wherein the second range of angular movement of the pivotable jaw is bound by the intermediate angle and a maximum angle relative to the fixed law such that the intermediate angle and the maximum angle of the pivotable jaw is defined between the pivotable and fixed jaws, and wherein the maximum angle is greater than the intermediate angle;

wherein the fixed jaw is configured to remain fixed parallel to the elongate shaft with the user input feature in the locked and unlocked state and as the pivotable jaw pivots through the first and second ranges of angular movement.

18. The apparatus of claim 15, wherein the maximum angle is at least ninety degrees, the intermediate angle is less than 180 degrees, and the minimum angle is between twenty-five degrees and sixty degrees.

19. The apparatus of claim 15, wherein the body comprises a handpiece having a trigger, wherein the trigger is operable to move the second jaw toward and away from the first jaw, wherein the user input feature is in communication with the trigger and is operable to selectively prevent movement of the trigger.

20. The apparatus of claim 15, wherein the trigger is movable relative to a grip member between a home position, an outward position, and an inward position, wherein the home position is associated with the intermediate angle, the outward position is associated with the maximum angle, and the inward position is associated with the minimum angle, wherein the user input feature is configured to lock the trigger in the outward position to prevent movement of the trigger from the home position toward the outward position, wherein the user input feature is configured to transition to a second locked state when the maximum angle is reached maintain the maximum angle between the jaws.

* * * * *